(12) United States Patent
Bevan et al.

(10) Patent No.: US 7,465,581 B2
(45) Date of Patent: Dec. 16, 2008

(54) ANKTM1, A COLD-ACTIVATED TRP-LIKE CHANNEL EXPRESSED IN NOCICEPTIVE NEURONS

(75) Inventors: Stuart Bevan, London (GB); Ardem Patapoutian, San Diego, CA (US); Gina M. Story, San Marcos, CA (US)

(73) Assignees: The Scripps Research Institute, La Jolla, CA (US); Novartis AG, Basel (CH)

( * ) Notice: Subject to any disclaimer, the term of this patent is extended or adjusted under 35 U.S.C. 154(b) by 240 days.

(21) Appl. No.: 10/539,377

(22) PCT Filed: Dec. 17, 2003

(86) PCT No.: PCT/EP03/14403

§ 371 (c)(1),
(2), (4) Date: Jan. 18, 2006

(87) PCT Pub. No.: WO2004/055054

PCT Pub. Date: Jul. 1, 2004

(65) Prior Publication Data

US 2006/0142547 A1    Jun. 29, 2006

Related U.S. Application Data

(60) Provisional application No. 60/434,540, filed on Dec. 18, 2002.

(51) Int. Cl.
*C12N 5/10* (2006.01)
*C12N 15/12* (2006.01)
*C12N 15/63* (2006.01)
*C12N 1/21* (2006.01)

(52) U.S. Cl. .................. 435/325; 435/69.1; 435/252.3; 435/320.1; 536/23.5

(58) Field of Classification Search ....................... None
See application file for complete search history.

(56) References Cited

OTHER PUBLICATIONS

Jaquemar et al. (1999). An ankyrin-like protein with transmembrane domains is specifically lost after oncogenic transformation of human fibroblasts. The Journal of Biological Chemistry. 274(11):7325-7333.*

* cited by examiner

*Primary Examiner*—Christine J Saoud
*Assistant Examiner*—Jon M Lockard
(74) *Attorney, Agent, or Firm*—DLA Piper LLP (US)

(57) ABSTRACT

The methods and compositions of the invention are based on a method for measuring nociceptive responses in vertebrates, including humans and other mammals utilizing a newly discovered thermoreceptor belonging to the Transient Receptor Potential (TRP) family of non-selective cation channels that participates in thermosensation and pain. This receptor, designated ANKTMI, is associated with nociceptive pain, such as hyperalgesia. Accordingly, the invention provides isolated polypeptides and polynucleotides associated with nociception as well as methods for identifying or screening agents that modulate nociception.

7 Claims, 10 Drawing Sheets

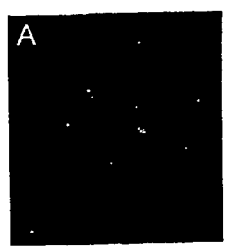 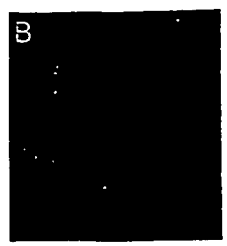 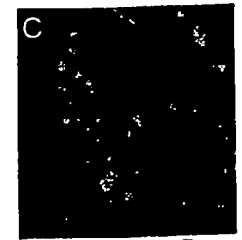
FIG. 3A  FIG. 3B  FIG. 3C
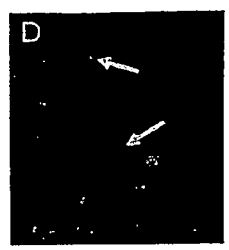 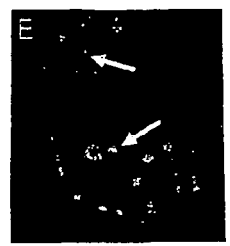 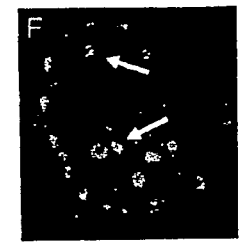
FIG. 3D  FIG. 3E  FIG. 3F
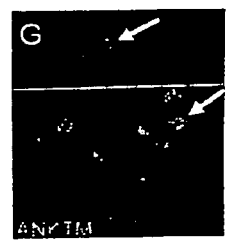  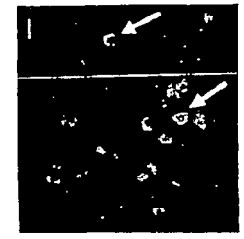
FIG. 3G  FIG. 3H  FIG. 3I
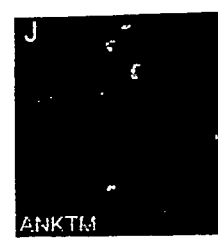 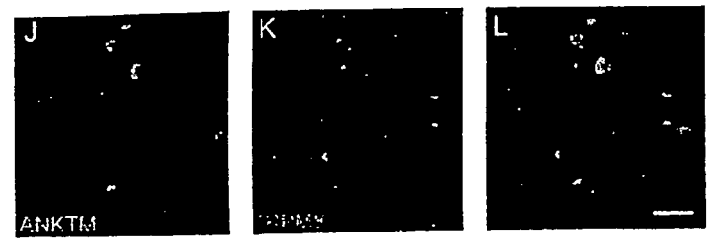 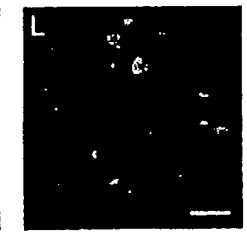
FIG. 3J  FIG. 3K  FIG. 3L
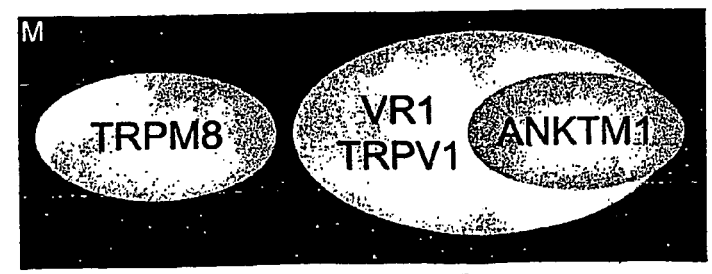
FIG. 3M mANKTM1 cds, 3.378 kb:

ATGAAGCGCGGCTTGAGGAGGATTCTGCTCCCGGAGGAAAGGAAGGAGGTC
CAGGGCGTTGTCTATCGCGGCGTCGGGGAAGACATGGACTGCTCCAAGGAAT
CCTTTAAGGTGGACATTGAAGGAGATATGTGTAGATTAGAAGACTTCATCAA
GAACCGAAGAAAACTAAGCAAATATGAGGATGAAATCTCTGTCCTCTGCAT
CACGCAGCAGCAGAAGGTCAAGTTGAACTGATGGAACTGATCATCAATGGTT
CTTCGTGTGAAGTGCTGAATATAATGGATGGTTATGGAAATACCCCACTGCAT
TGTGCTGCAGAAAAAATCAAGTTGAAAGTGTAAAGTTTCTTCTCAGCCAAG
GAGCAAATCCAAACCTCCGAAATAGAAACATGATGTCACCCCTTCACATAGC
TGTGCATGGCATGTACAACGAAGTGATCAAGGTGTTGACTGAGCACAAGGCC
ACTAACATCAATTTAGAAGGAGAGAATGGGAACACGGCTTTGATGTCCACGT
GTGCCAAAGACAACAGTGAAGCTTTGCAAATTTTGTTAGAAAAAGGAGCTAA
GCTGTGTAAATCAAATAAGTGGGGAGACTACCCTGTGCACCAGGCAGCATTT
TCAGGTGCCAAAAAATGCATGGAATTAATCTTAGCATATGGTGAAAAGAACG
GCTACAGCAGGGAGACTCACATTAATTTTGTGAATCACAAGAAAGCCAGCCC
TCTCCACCTAGCAGTTCAAAGCGGAGACTTGGACATGATTAAGATGTGCCTG
GACAACGGTGCACACATCGACATGATGGAGAATGCCAAATGCATGGCCCTCC
ATTTTGCTGCAACCCAGGGAGCCACTGACATCGTTAAGCTCATGATCTCATCC
TATACCGGAAGTAGTGATATTGTGAATGCAGTTGATGGCAATCAGGAGACCC
TGCTTCACAGAGCCTCGTTATTTGATCACCATGACCTGGCAGAATACCTAATA
TCAGTGGGAGCAGACATCAACAGCACTGATTCTGAAGGACGCTCTCCACTTA
TTTTAGCAACAGCTTCTGCATCCTGGAACATTGTGAATTTGCTCCTCTGTAAA
GGTGCCAAAGTAGACATAAAAGATCATCTTGGACGTAACTTTTTGCATTTGAC
TGTGCAGCAGCCTTATGGACTAAGAAATTTGCGGCCTGAGTTTATGCAGATG
CAACACATCAAAGAGCTGGTGATGGATGAAGACAATGATGGATGCACACCTC
TCCATTATGCCTGTAGGCAGGGGGTTCCTGTCTCTGTAAATAACCTCCTTGGC
TTCAATGTGTCCATTCATAGCAAAAGTAAAGATAAGAAGTCGCCCCTGCATTT
TGCAGCCAGTTATGGGCGCATCAATACATGTCAGAGACTTCTGCAAGACATA
AGTGATACGAGGCTTTTGAATGAAGGGGATCTCCATGGGATGACCCCTCTCC
ACCTGGCAGCAAAAAATGGGCATGATAAAGTCGTTCAACTCCTTCTGAAGAA
AGGGGCCTTATTTCTCAGTGACCACAATGGCTGGACTGCTTTGCATCACGCCT
CCATGGGTGGGTACACTCAGACCATGAAGGTCATTCTTGATACTAACTTGAA
ATGCACAGACCGACTAGATGAAGAAGGGAACACAGCACTCCACTTTGCAGCA
CGGGAAGGCCATGCCAAGGCTGTTGCAATGCTTTTGAGCTACAATGCTGACA
TCCTCCTGAACAAGAAGCAAGCTTCCTTTCTGCATATTGCCCTGCACAATAAG
CGCAAGGAAGTGGTTCTCACAACCATCAGAAATAAAAGATGGGATGAGTGTC
TTCAAGTTTTCACTCATAATTCTCCAAGCAATCGATGTCCAATCATGGAGATG
GTAGAATACCTCCCCGAGTGCATGAAAGTTCTTTTAGATTTCTGCATGATACC
TTCCACAGAAGACAAGTCCTGTCAAGACTACCATATTGAGTATAATTTCAAGT
ATCTCCAATGCCCATTATCCATGACCAAAAAAGTAGCACCTACCCAGGATGT
GGTATATGAGCCTCTTACAATCCTCAATGTCATGGTCCAACATAACCGCATAG

FIG. 8A

```
AACTCCTCAACCACCCTGTGTGTAGGGAGTACTTACTCATGAAATGGTGTGCC
TATGGATTCAGAGCCCATATGATGAACCTAGGATCTTATTGTCTTGGTCTCAT
ACCCATGACCCTTCTTGTTGTCAAAATACAGCCTGGAATGGCCTTCAATTCTA
CTGGAATAATCAATGGAACTAGTAGTACTCATGAGGAAAGAATAGACACTCT
GAATTCATTTCCAATAAAAATATGTATGATTCTAGTTTTTTTATCAAGTATATT
TGGATATTGCAAAGAAGTGATCCAAATTTTCCAACAGAAAAGGAATTACTTC
CTGGATTACAACAATGCTCTGGAATGGGTTATCTATACAACTAGTATCATCTT
CGTGTTGCCCTTGTTCCTCAACATCCCAGCGTATATGCAGTGGCAATGTGGAG
CAATAGCGATATTCTTCTACTGGATGAACTTCCTACTGTATCTTCAAAGGTTT
GAGAACTGTGGAATTTTCATTGTTATGTTGGAGGTGATTTTTAAAACATTGCT
GAGATCGACCGGAGTGTTTATCTTCCTCCTACTGGCTTTTGGCCTCAGCTTTTA
TGTTCTCCTGAATTTCCAAGATGCCTTCAGCACCCCATTGCTTTCCTTAATCCA
GACATTCAGTATGATGCTAGGAGACATCAATTATCGAGATGCCTTCCTAGAA
CCATTGTTTAGAAATGAGTTGGCATACCCAGTCCTGACCTTTGGGCAGCTTAT
TGCCTTCACAATGTTTGTCCCAATTGTTCTCATGAACTTACTGATTGGCTTGGC
GGTTGGGGACATTGCTGAGGTCCAGAAGCATGCGTCATTGAAGAGGATTGCT
ATGCAGGTGGAACTTCATACCAACTTAGAAAAAAGCTGCCACTCTGGTACT
TACGCAAAGTGGATCAGAGGTCCACCATCGTGTATCCAAATAGACCCAGGCA
CGGCAGGATGCTACGGTTTTTCATTACTTTCTTAATATGCAAGAAACACGAC
AAGAAGTACCAAACATTGACACATGCTTGGAAATGGAAATATTGAAACAGAA
ATATCGGCTGAAGGACCTCACTTCCCTCTTGGAAAAGCAGCATGAGCTCATC
AAACTCATCATCCAGAAGATGGAGATCATCTCAGAGACAGAAGATGAAGATA
ACCATTGCTCTTTCCAAGACAGGTTCAAGAAGGAGAGGCTGGAACAGATGCA
CAGCAAGTGGAATTTTGTCTTAAACGCAGTTAAGACTAAAACACATTGTTCTA
TTAGCCACCCGGACTTTTAG
```

ANKTM1, A COLD-ACTIVATED TRP-LIKE CHANNEL EXPRESSED IN NOCICEPTIVE NEURONS

CROSS REFERENCE TO RELATED APPLICATIONS

This application is a 35 USC § 371 National Stage application of PCT Application No. PCT/EP2003/014403 filed Dec. 17, 2003; which claims the benefit under 35 USC § 119(e) to U.S. Application Ser. No. 60/434,540 filed Dec. 18, 2002. The disclosure of each of the prior applications is considered part of and is incorporated by reference in the disclosure of this application.

ACKNOWLEDGMENT OF GOVERNMENT SUPPORT

This invention was made in part with government support under NINDS Grant No. R01NS42822 awarded by the National Institutes of Health. The federal government may have certain rights in this invention.

FIELD OF THE INVENTION

The invention relates generally to nociceptive pain and disorders associated with pain and more specifically to polynucleotides encoding polypeptides that affect nociceptive pain and methods for use therefor.

BACKGROUND

Pain has been defined in a variety of ways. For example, pain can be defined as the perception by a subject of noxious stimuli that produces a withdrawal reaction by the subject. The most commonly experienced form of pain may be defined as the effect of a stimulus on nerve endings, which results in the transmission of impulses to the cerebrum. This somatic sensation and normal function of pain, referred to as nociception or nociceptive pain, informs the organism of impending tissue damage. Somatic and visceral free nerve endings, termed nociceptors, initially process such pain signals.

Pain is a subjective experience related to perception of inputs to the central nervous system by a specific class of sensory receptors known as nociceptors. Nociceptors fire in response to noxious thermal, mechanical and chemical stimuli. Coding of a stimulus as painful occurs at several levels in the nervous system. The first is at the level of transduction of the noxious stimulus in the peripheral nerve terminals of the nociceptors. During the transduction step, the noxious stimulus is converted to an electrical stimulus in the form of an action potential. In mammals the vanilloid receptors (VR-1 and VRL-1) are proposed to function during transduction of a noxious heat stimulus. Candidate molecules for transducing noxious mechanical stimuli have yet to be identified.

The second level of coding occurs in the dorsal horn of the spinal cord. The cell bodies of nociceptive neurons are found in the dorsal root ganglia and send projections both to the periphery and to the dorsal horn. Upon stimulation nociceptors release the excitatory neurotransmitter glutamate, among others, which produces action potential sin post-synaptic cells of the dorsal horn, which project to the brain where pain is perceived. The higher level processing involved in pain perception is poorly understood. High intensity pain is signaled through increased release of substance P by the afferent nociceptive terminals in the dorsal horn. This peptide function through the G-protein couples substance P receptor, NK-1.

In general, while brain pathways governing the perception of pain are still incompletely understood, sensory afferent synaptic connections to the spinal cord, termed "nociceptive pathways" have been studied. The nociceptive pathway, which exists for protection of the organism (such as the pain experienced in response to a burn or noxious cold), is inactive. Activity is initiated by the application of a high intensity, potentially damaging stimulus. This stimulus serves to depolarize certain classes of afferent (sensory) axons of the small unmyelinated category, designed C fibers.

The signal carried by the C fibers travels up the peripheral nerve and into the spinal cord where synapses are made on second order and higher order neurons, which then transmit the pain signal up the spinal cord in the spinothalamic tract ending in the thalamus. Polysynaptic junctions in the dorsal horn of the spinal cord are involved in the relay and modulation of sensations of pain to various regions of the brain, including the periaqueductal grey region. The ventrolateral and ventromedial thalamic nuclei project to the cortex where the pain is then processed with regard to localization and other integrative characteristics.

Analgesia, or the reduction of pain perception, can be affected directly by decreasing transmission along such nociceptive pathways. Analgesic opiates are thought to act by mimicking the effects of endorphin or enkephalin peptide-containing neurons, which synapse presynaptically at the C-fiber terminal and which, when they fire, inhibit release of substance P from the C-fiber. Descending pathways from the brain are also inhibitory to C-fiber firing. Thus, CNS-mediated analgesia leads to an overall inhibition of the pain transmission.

While neuropathic pain is known to have a number of underlying etiologies, it is characterized by a distinct set of symptoms. As described in greater detail below, these can include enhanced sensitivity to innocuous thermal-mechanical stimuli, abnormal sensitivity to noxious stimuli, tenderness, and spontaneous burning pain. Neuropathic pain is also progressive in nature, in that it generally worsens over time. Known treatment methods treat the symptoms without necessarily lessening the underlying pathology.

Typically, chronic nociceptive pain results from changes in the peripheral sensory terminal secondary to local tissue damage. Mild damage, such as abrasions or burns, and inflammation in the cutaneous receptive fields or joints will produce significant increases in the excitability of polymodal nociceptors (C fibers) and high threshold mechanoreceptors. This increased excitability leads to increased spontaneous activity and an exaggerated response to otherwise minimal stimuli.

These events have several consequences. First, the magnitude of the pain state in humans and animals is proportional to the discharge rate in such sensory afferent. The facilitated response secondary to the local peripheral injury may lead to an exaggerated pain state simply because of the increased afferent activity. Secondly, spontaneous activity in small sensory afferent causes central neurons in the spinal cord to develop an exaggerated response to subsequent input. Both of these events, secondary to the increased spontaneous activity and reactivity in small sensory afferent generated by the peripheral injury leads to a behavioral state referred to as hyperalgesia. Thus, where the pain response is the result of an exaggerated response to a given stimulus, the organism is hyperalgesic. The importance of the hyperalgesic state in the post injury pain state has been repeatedly demonstrated and this facilitated processing appears to account for a major proportion of the post-injury/inflammatory pain state.

Despite numerous definitions, the brain pathways, mechanisms and intermediates governing the perception of pain are not completely understood. A number of analgesics and opiates are currently on the market to address the discomforts associated with pain. However, many of these agents are addictive or have side effects that often provide additional discomforts to a subject when taken over a long period of time. For example, side effects associated with a number of opiates include sedation, depression of respiration, constipation, nausea and emesis, abuse liability and the development of addiction. These effects serve to limit the utility of opiates for controlling post injury pain. Addiction liability can occur secondary to medical uses of the drug where the central effects lead to an addicted and dependent state.

The ability to sense cold as a distinct presence resides in specialized neurons within the peripheral nervous system that detect varied environmental temperature. The cell bodies of these sensory neurons reside in the vertebral column and their projections extend for long distances to peripheral tissues such as the skin. It is hypothesized that channels present at the end of these projections are activated by physical stimuli such as temperature and pressure (Hensel, Monogr Physiol Soc 38:1-321, 1981).

The cloning of TRPV1 (VR1: a capsaicin- and heat-activated channel) has proven this hypothesis and ignited research into thermosensation at the molecular level (Caterina et al., Nature 389:816-824, 1997). TRPV1 is activated near 43° C., a temperature most mammals find noxious. Three other TRPV channels with greater than 40% amino-acid level identity to TRPV1 have since been cloned and characterized as thermosensors. These channels are activated at various heat thresholds, ranging from 33° C. (warm) for TRPV3 to 55° C. (high-threshold noxious heat) for TRPV2 (Caterina et al., Nature 398, 436-441, 1999; Peier et al., Science 296: 2046-2049, 2002b; Smith et al., Nature 418:186-190, 2002; Xu et al., Nature 418:181-186, 2002). TRPV4, originally described as an osmo-sensor, has also been shown to be activated by warm temperatures. Much less is known about channels that sense cold. Recently, the cloning of a menthol- and cold-activated channel, TRPM8 (CMR1) was described (McKemy et al., Nature 416:52-58, 2002; Peier et al., Cell 108:705-715, 2002a). The threshold of TRPM8 activation is reported to be either 28° C. or 23° C., consistent with the pleasant/cool feeling that menthol products convey. Since TRPM8 is mostly activated at cool rather than cold temperatures, it has been postulated that other cold-activated channels exist.

The known thermoreceptors all belong to the Transient Receptor Potential (TRP) family of non-selective cation channels. TRP channels are divided into three subclasses designated TRPC, TRPV, and TRPM (Montell et al., Mol Cell 9:229-231, 2002). All have six putative transmembrane domains with a proposed pore region between transmembrane domains five and six. TRP channels are thought to have cytoplasmic N- and C-termini. The three classes of TRP channels are distinguished according to overall homology as well as a few unique characteristics. TRPV and TRPC members contain two to four N-terminal ankyrin domains thought to be involved in linking transmembrane proteins to the cytoskeleton. TRPC and TRPM members have a TRP box (with unknown function) following the sixth transmembrane domain. The involvement of TRP channels in sensory function has been evident from the beginning. It is now recognized that several other classes of ion channels are homologous to the classical TRP channels and a new nomenclature system has been proposed to reflect this relationship (Montell, 2001, supra). The new subtypes include TRPP for PKD2-like channels (PKD2 is mutated in polycystic kidney disease), TRPML for Mucolipidin-like channels (Mucolipidin mutations are responsible for some lysosomal storage disorders), and TRPN for NOMPC-like channels, which are distinguished by a large number of N-terminal ankyrin repeats (NOMPC is required for mechanosensory function in flies).

Pain is a major problem for the individual sufferer and for society because of the high costs involved in managing pain. Pain is often a part of numerous disorders or diseases including, for example, cancer pathology. Terminally ill subjects often suffer immensely because our ability to effectively manage pain is inadequate. Therefore, strategies to identify molecules that function in pain sensation are needed.

SUMMARY OF THE INVENTION

In one embodiment, the invention provides isolated nucleic acid sequences encoding an ANKTM1-related polypeptide, which are characterized as encoding a temperature/pain sensitive non-selective cation channel protein that is activated by temperature below 20° C.; being expressed in Calcitonin gene-related peptide- and substance P-positive neurons. The invention nucleic acid sequences comprise more than five ankyrin domains and a six transmembrane domain.

In another embodiment, the invention provides methods for identifying an agent that modulates nociceptive response by contacting an organism containing an ANKTM1-related polypeptide encoded by an invention nucleic acid sequence with an agent suspected of having nociceptive pain modulating activity under conditions that allow the agent and the polypeptide to interact. A nociceptive stimulus is then administered to the organism and any nociceptive response is measured and compared with the nociceptive response of the organism to the stimulus when not administered the agent. A change in the nociceptive response indicates the agent modulates the nociceptive response to the stimulus.

In yet another embodiment, the invention provides methods for modulating nociceptive pain in a sentient organism that contains a polypeptide sequence comprising an amino acid sequence selected from SEQ ID NO:1, SEQ ID NO:2 and SEQ ID NO:4, and conservative variations thereof by contacting the organism with an effective amount of an agent that modulates operation of the polypeptide under conditions that allow the agent and the polypeptide to interact, thereby modulating nociceptive pain in the organism.

In still another embodiment, the invention provides methods for reducing nociceptive pain in an organism by contacting an organism containing an invention isolated nucleic acid sequence with an effective amount of an agent that blocks function of the polynucleotide sequence under conditions that allow the agent and the polynucleotide to interact, thereby reducing nociceptive pain in the organism.

BRIEF DESCRIPTION OF THE FIGURES

FIG. 1A is a representation of a phylogenetic tree of TRP channels showing ANKTM1 grouped together with an emerging group of TRP-like channels that have multiple ankyrin domains (more than eight) and a six unit transmembrane (TM) domain. To date, ANKTM1 is the only vertebrate member of this family (mouse=mANKTM1 (SEQ ID NO:1) and human=hANKTM1 (SEQ ID NO:2). A close homologue exists in *Drosophila* that is designated dmANKTM1 (SEQ ID NO:3). Overall, four *drosophila* (dm) (including NOMPC) members and two *C. elegans* (ce) family members belong to this family (dmNOMPC (SEQ ID NO:4); ceNOMPC (SEQ ID NO:5); ce(NP_502249) (SEQ ID NO:6); dm(CG1-409) (SEQ ID NO:7); dm(CG17142) (SEQ ID NO:8). Similarities are calculated in Blast2.

FIGS. 1B and 1C show an alignment comparison of amino acid sequences (SEQ ID NOs:1-8) from the putative transmembrane domains of proteins in the phylogenetic tree shown in FIG. 1A. The alignment shows strong similarity in areas such as transmembrane domain six (TM6) among all members, and more specific pockets of similarity common to the three ANKTM1 homologues peppered throughout the region. The alignment is generated using MEGALIGN™ and BOXSHADE™ alignment programs. Identical and conserved areas are shaded. Transmembrane domains of mANKTM1 are marked as TM.

FIG. 3 shows the results of in-situ hybridization and immunostaining analyses, which demonstrate ANKTM1 expression in a subset of TRPV1-positive nociceptive DRG neurons.

(A-C) ANKTM1 mRNA is not present in heavily myelinated neurons marked by Neurofilament (NF 150) antibody. (D-F) ANKTM1 and calcitonin-gene-related peptide (CGRP) are coexpressed (arrows D-F). (G-L) Double-in situ hybridization shows ANKTM1 is present in a sub-population of thermosensitive neurons expressing TRPV1 (arrows G-I), but not TRPM8. Size bar is 50 µm. (M) A schematic representation showing that ANKTM1 is expressed in a subset of TRPV1-positive nociceptive DRG neurons and in a sub-population of thermosensitive neurons expressing TRPV1, but not TRPM8.

Figure 4A:
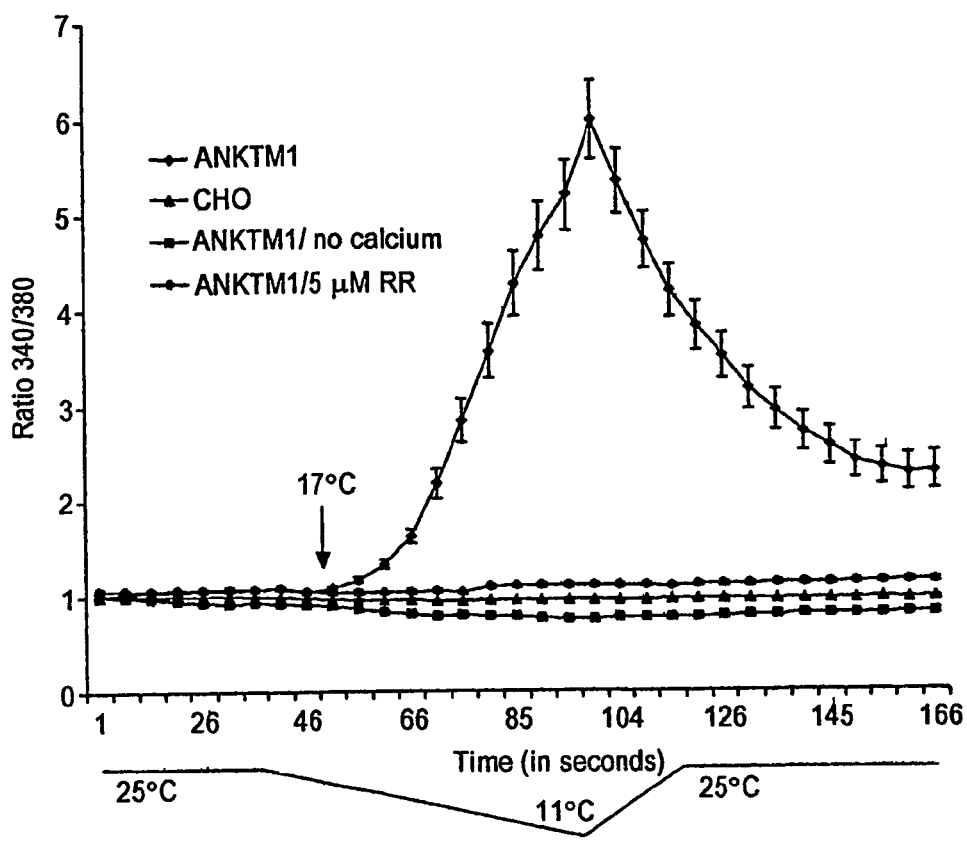

FIG. 4A is a graph showing that ANKTM1 is a calcium permeable cation channel that responds to a cold stimulus by eliciting a rise in $[Ca^{2+}]_i$ in ANKTM1-expressing CHO cells. A schematic representation of the stimulus temperature is indicated below the graph. CHO=untransfected CHO cells; RR=ruthenium red blocker. Values shown are average increase in ratio 340/380±SEM of 30-40 cells from representative experiments.

Figure 4B:
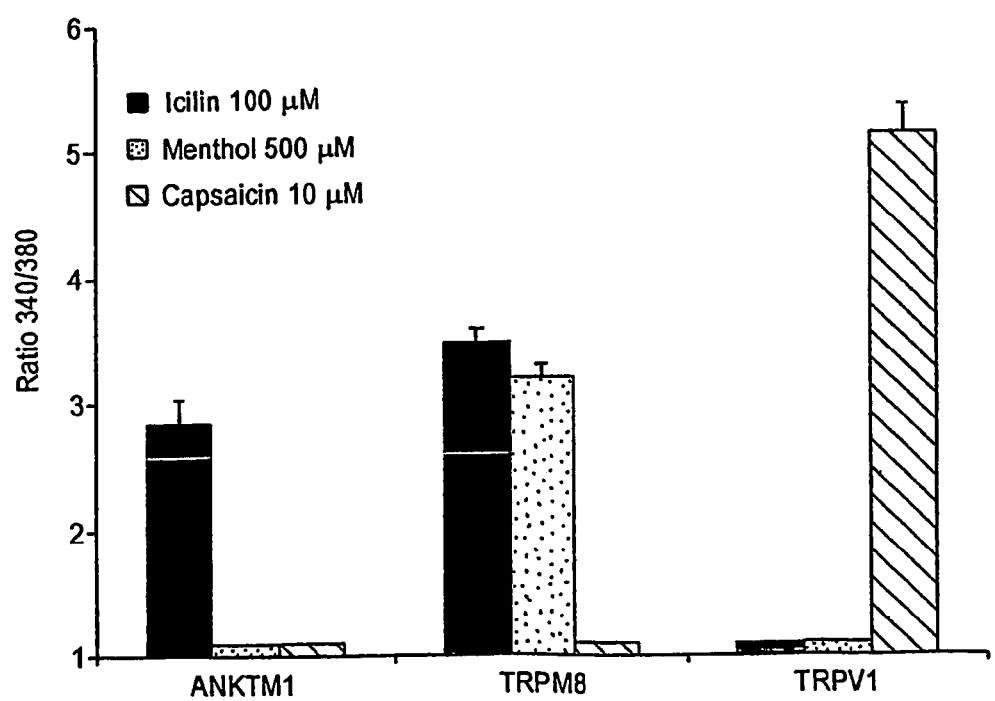

FIG. 4B is a graph showing average fold increase in 340 nm/380 nm ratio of ANKTM1-, TPRM8-, and TRPV1-expressing CHO cells in response to hot- (capsaicin) and cold- (menthol, icilin) inducing compounds.

Figure 5A:
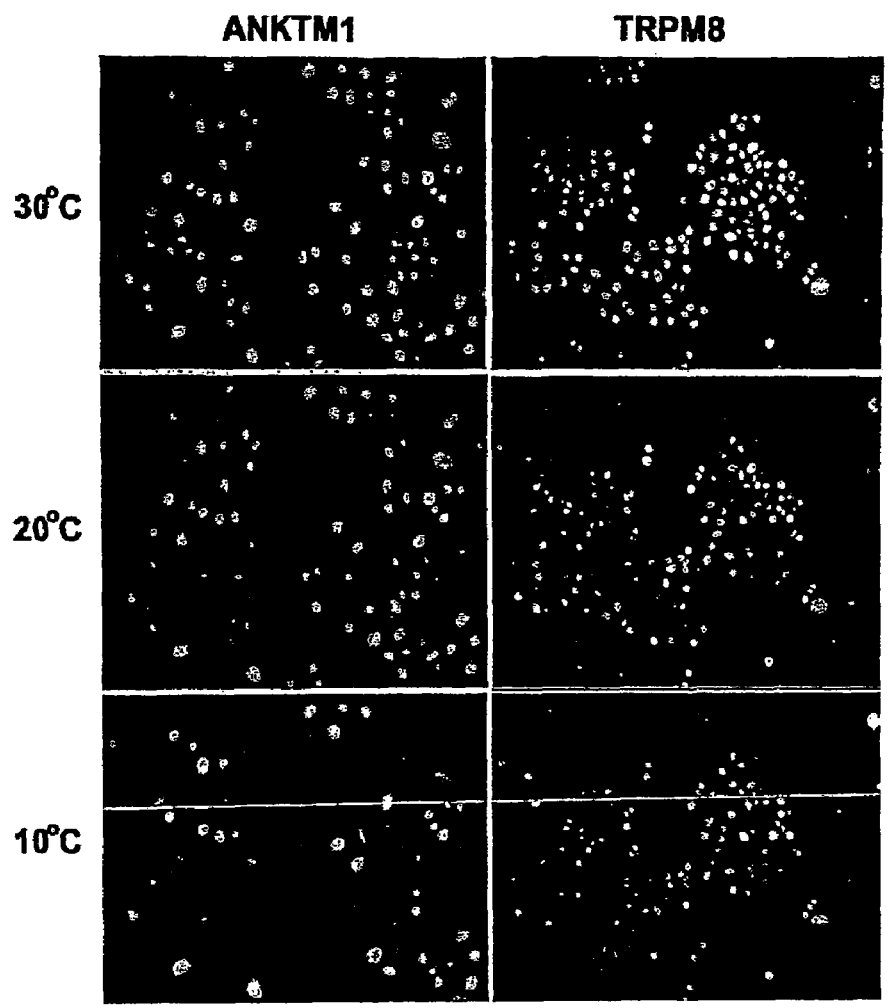

FIGS. 5A and B show that ANKTM1 is activated at colder temperatures compared to TRPM8.

FIG. 5A shows representative images taken from calcium imaging experiments comparing responses to gradual cooling of Fura-2 loaded ANKTM1- and TRPM8-expressing CHO cells. Increases in fluorescence correspond to increases in intracellular calcium levels and are indicated by a change in color where red>yellow>green>blue. Note that the majority of ANKTM1-expressing cells (left) are not active until temperatures fall below 20° C., while many TRPM8 expressing cells (right) are already strongly activated at 20° C.

Figure 5B:
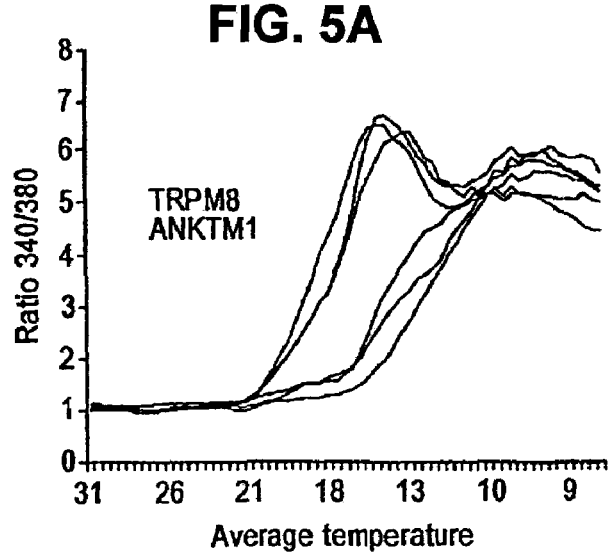

FIG. 5B is a graph showing responses of individual ANKTM1- and TRPM8-expressing CHO cells to gradual cooling from 31° C. to 9° C. Responses shown are from representative cells.

FIGS. 6A-D are a series of graphs showing currents evoked by decreasing temperatures in CHO cells expressing ANKTM1.

Figure 6A:
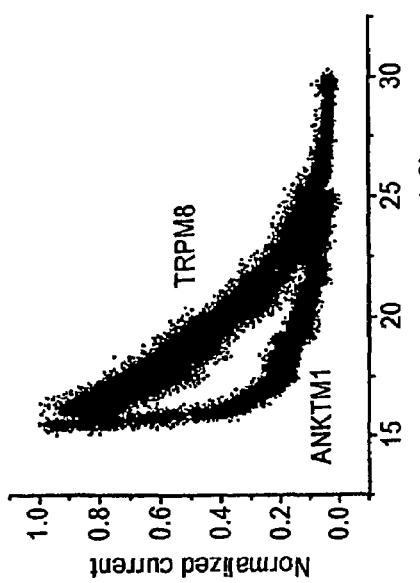

FIG. 6A provides an example of an inward current evoked by cooling of a cell voltage clamped at −60 mV.

Figure 6B:
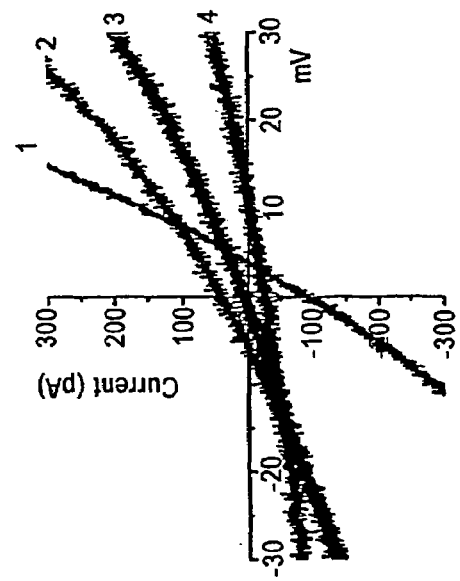

FIG. 6B is a graph showing a comparison of temperature current relationship for ANKTM1 and TRPM8. The threshold for activation of ANKTM1 is lower than that of TRPM8.

Figure 6C:
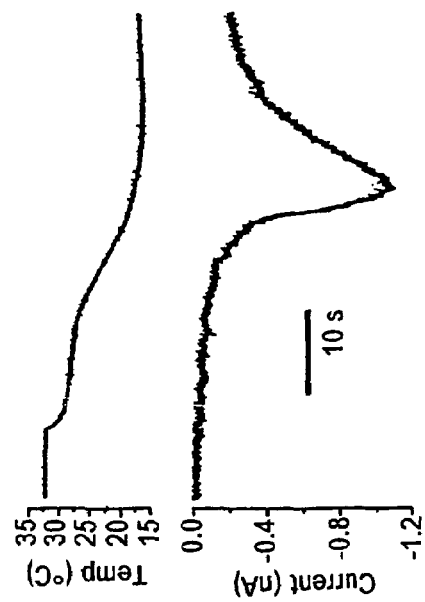

FIG. 6C is a graph showing current-voltage relationship for ANKTM1 (voltage ramp is from −100 mV to +80 mV with two second ramps). The current is outwardly rectifying and there is an increase in both inward and outward currents when the temperature is lowered (30° C.-18° C.).

Figure 6D:
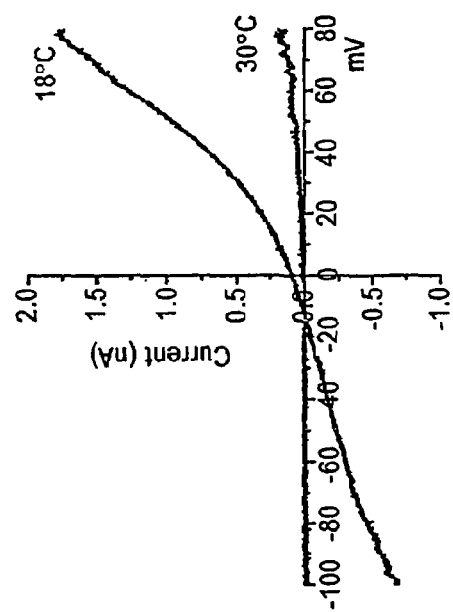

FIG. 6D is a graph showing current-voltage relationships for ANKTM1 in various external solutions. The main charge ion is (1) 140 mM NaCl (2) 40 mM NaCl/100 mM choline (3) 1 mM CaCl (4) 30 mM CaCl. $E_{revs}$ for these examples are, +4, −6, −2 and +11 mV, respectively.

FIGS. 7A-D are a series of graphs showing that ANKTM1 currents are desensitized to repeated cold stimuli.

Figure 7A:
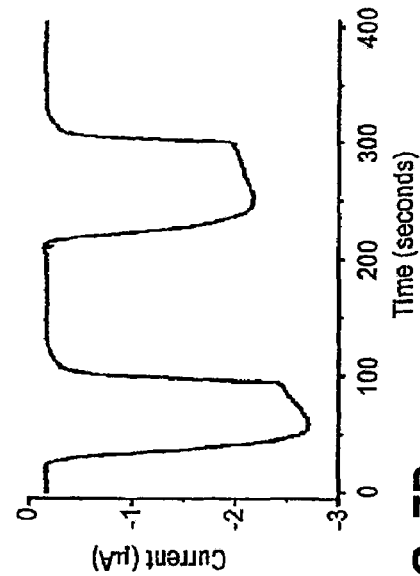
Figure 7C:
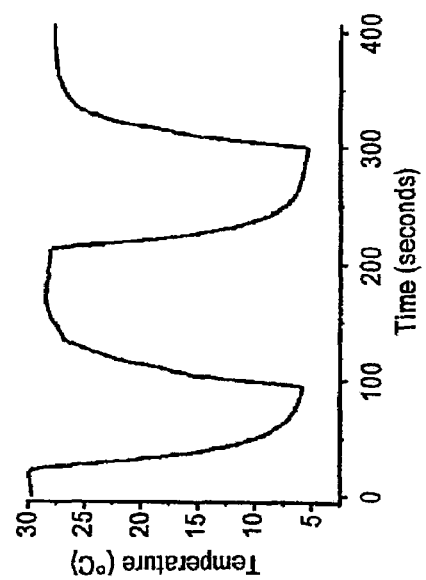

FIGS. 7A and 7C show, respectively, inward currents recorded in response to first and second cold steps from *Xenopus* oocytes expressing ANKTM1.

Figure 7B:
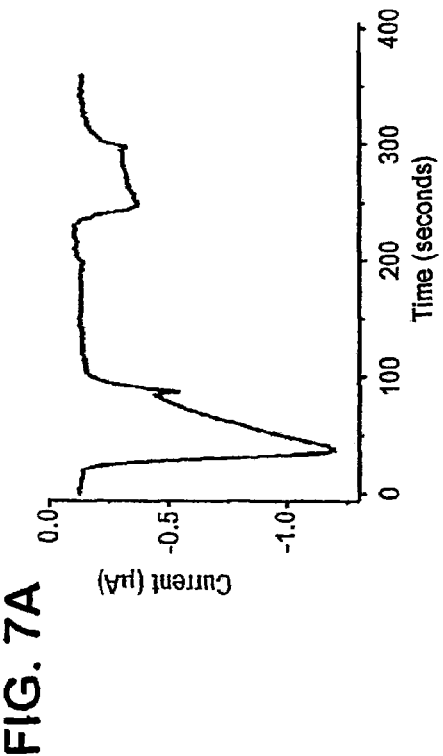
Figure 7D:
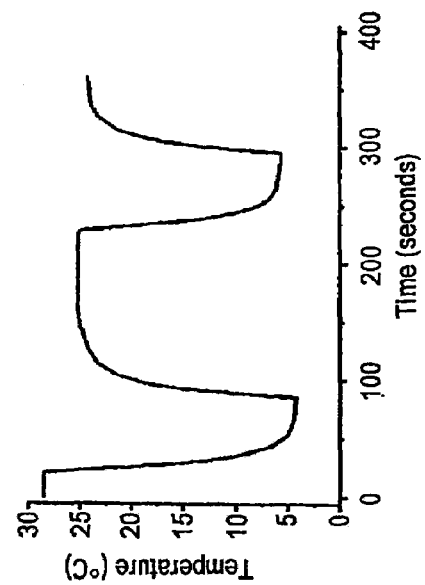

FIGS. 7B and 7D show, respectively, inward currents recorded in response to cold steps from *Xenopus* oocytes expressing TRPM8. The oocytes were held at −70 mV during the recordings. ANKTM1 current responses were markedly reduced in the second cold step.

FIGS. 8A and 8B show the nucleotide sequence (SEQ ID NO:13) of the 3.378 kb mouse homologue (mANKTM) of human ANKTM (hANKTM).

DETAILED DESCRIPTION OF THE INVENTION

In humans and other vertebrates, painful stimuli are sensed by specialized neurons known as nociceptors, which fire in response to noxious temperature and mechanical or chemical stimuli, all of which have the potential to cause tissue damage. The signals are in turn processed by the central nervous system and perceived as pain, serving an indispensable protective role. Nociceptors are also involved in pathological pain states caused by inflammation, nerve damage, or cancer. An increased understanding of nociception therefore is of wide interest, and model systems for molecular genetic analysis are desirable.

The methods and compositions of the invention are based on a method, described herein, to measure nociceptive responses in vertebrates such as, for example, mammals including humans, utilizing a new member of the TRPN family that participates in thermosensation and pain. This receptor, designated ANKTM1, is associated with nociceptive pain. Accordingly, the invention provides isolated polypeptides and polynucleotides associated with nociception as well as methods for identifying or screening agents that modulate nociception.

As used herein, "hyperalgesia" or a "hyperalgesic state" refers to a condition in which a warm-blooded animal is extremely sensitive to mechanical, chemical or thermal stimulation that, absent the condition, would be painless. Typical models for such a hyperalgesic state include the inflamed rat paw compression model and the compression of the inflamed knee joint.

Hyperalgesia is known to accompany certain physical injuries to the body, for example the injury inevitably caused by surgery. Hyperalgesia is also known to accompany certain inflammatory conditions in man such as arthritic and rheumatic disease. Hyperalgesia, thus refers to mild to moderate pain to severe pain such as the pain associated with, but not limited to, inflammatory conditions (e.g., such as rheumatoid arthritis and osteoarthritis), postoperative pain, postpartum pain, the pain associated with dental conditions (e.g., dental caries and gingivitis), the pain associated with burns, including but not limited to sunburns, abrasions, contusions and the like, the pain associated with sports injuries and sprains, inflammatory skin conditions, including but not limited to poison ivy, and allergic rashes and dermatitis, and other such pain that increases sensitivity to mild stimuli, such as cold.

To date, all five thermo-activated channels identified belong to the TRP family, characterized by six transmembrane domains (all) and N-terminal ankyrin domains (most) (Montell, 2001, supra). In the invention, a combined bioinformatic and expression analysis approach has been used to identify additional TRP channels involved in sensory detection. A search in PFAM protein sequence HMM data base for predicted cDNA sequences that contain both ankyrin domains (PFAM00023) and six-transmembrane domains (PFAM00520) led to ANKTM1. Human ANKTM1 is an uncharacterized putative channel cloned from cultured fibroblasts. A previous study had shown no significant expression of ANKTM1 in various tissues examined, although EST sequences suggest that ANKTM1 is upregulated in many human tumor cells (Jaquemar et al., J Biol Chem 274:7325-7333, 1999).

To characterize human ANKTM1, full-length mouse ANKTM1 was amplified from mouse dorsal root ganglia (DRG) and trigeminal ganglia that contain somatic sensory neurons using RT-PCR. Theoretical translation of the mouse nucleotide sequence predicts a protein of 1125 amino acid residues, very similar to human ANKTM1 (1119 amino acids). Mouse ANKTM1 has 14 predicted N-terminal ankyrin domains followed by a six transmembrane (6TM) domain (see FIG. 1A).

Figures 1A, 1B-1:
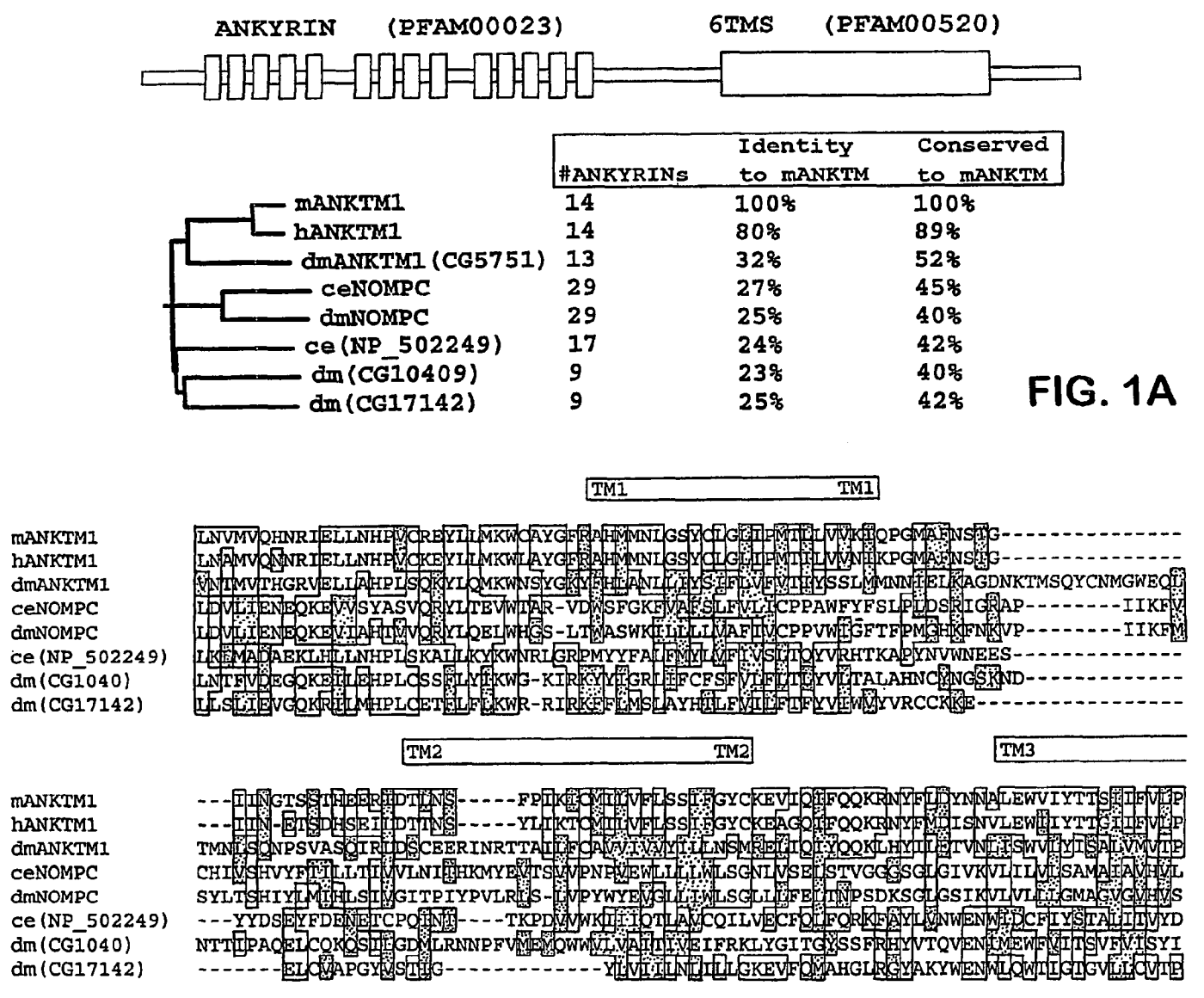
Figure 1C:
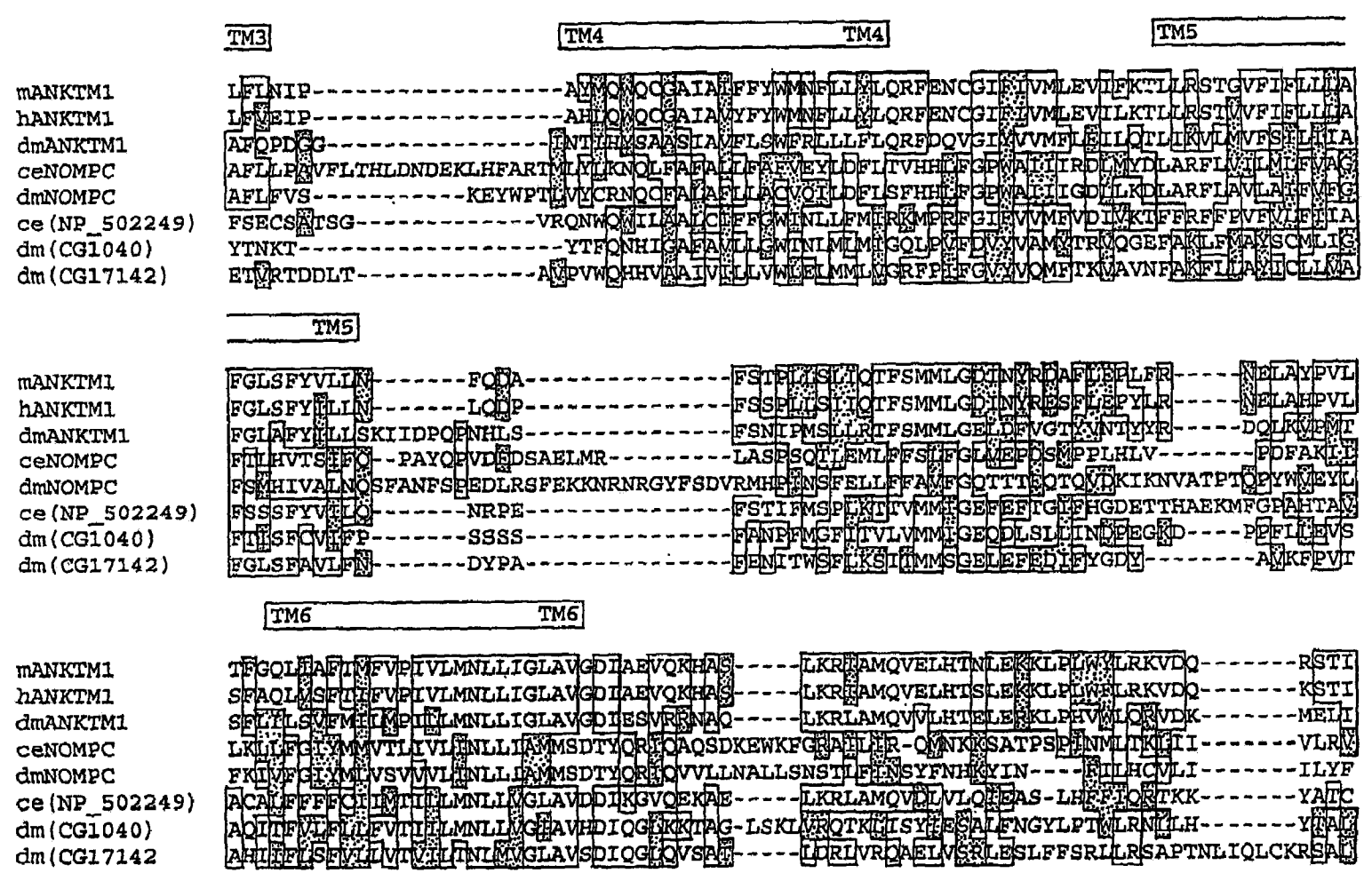

A phylogenetic tree analysis of all TRP-like channels grouped ANKTM1 with Drosophila NOMPC, which has 29 N-terminal ankyrin domains and is required for mechanosensation (Walker et al., Science 287:2229-2234, 2000). Further searches for proteins that contain both a 6TM domain and more than five ankyrin domains (to exclude TRPV and TRPC members, which have two to four ankyrin domains) demonstrated that ANKTM1 is the only mammalian member of this group. Drosophila has four such proteins dmANKTM1 (SEQ ID NO:3), dmNOMPC (SEQ ID NO:4), dmCG10409 (SEQ ID NO:7) and dmCG17142 (SEQ ID NO:8). In C. elegans two such proteins have been found, ceNOMPC (SEQ ID NO:5) and ceNP-502249 (SEQ ID NO:6) (FIGS. 1A and B). These putative channels form a branch of TRP proteins named TRPN after the founding member, NOMPC. Some of the TRPN family members do not have high similarity at the primary amino acid level: mANKTM1 (SEQ ID NO:1) shares only 25% amino acid identity to dmNOMPC (SEQ ID NO:4). By comparison, TRPV1 and TRPV3 are 43% similar. The clustering of mANKTM1 and NOMPC in the phylogenetic tree reflects their shared numerous N-terminal ankyrin domains. Indeed, if 6TM domains alone are compared, ANKTM1 is more similar to TRPV3 than to NOMPC. Therefore, the phylogenetic tree organization should be carefully interpreted.

However, at the amino-acid level, the two cold-receptors surprisingly have no significant amino acid sequence identity. This finding is in contrast to the four heat-activated TRPV channels, which have at least 40% amino acid sequence identity. The transmembrane domain of ANKTM1 is more similar to TRPV members than to any other mammalian proteins. This amino acid similarity is likely significant at the structural level since ruthenium red, a potent blocker of all TRPV channels, also blocks ANKTM1. The 16 N-terminal ankyrin domains show further correlation with TRPV channels (two to four ankyrin domains). However, in phylogenetic tree prediction programs, ANKTM1 is grouped with the emerging TRPN family of NOMPC-like channels, probably due to the large number of N-terminal ankyrin domains reported in this family. Within this group of putative channels, the uncharacterized protein CG5751 is shown to be the Drosophila orthologue of ANKTM1, since the two proteins are more similar to each other than to any other protein.

Most TRP channels are non-selective cation channels and readily let calcium into cells when activated, permitting both electrophysiological studies and intracellular calcium imaging. Therefore, in the studies described herein a series of intracellular calcium imaging and electrophysicological studies were applied to ANKTM1. Fluorescence microscopy was used to monitor increases in intracellular calcium concentration in response to various sensory stimuli by loading ANKTM1-expressing CHO cells with the calcium indicator fluorescent dye, Fura-2. Hypo-osmotic solutions are known to elicit calcium influx in TRPV4-expressing cells. However, when ANKTM1 was subjected to hypo-osmotic solution, activation did not occur. Heat stimuli of up to 42° C. and 52° C. are strong activators of TRPV1 and TRPV2 respectively (Caterina et al., 1999; supra; Caterina et al., 1997, supra). However, ANKTM1-expressing CHO cells, when stimulated with heat in this range, were not activated. Menthol or cool stimuli in the range of 23-28° C., the threshold of activation of TRPM8 (McKemy et al., 2002, supra; Peier et al., 2002b, supra), also failed to activate ANTKM1.

However, it was discovered that lowering temperature to 10° C. caused a large influx of calcium in ANKTM1-expressing cells, but not in Tet-treated CHO cell controls (FIG. 4A). This response to cold stimulus by ANKTM1 was abolished upon removal of extracellular calcium, showing that ANKTM1 is acting as a calcium permeable channel rather than releasing calcium from intracellular stores (FIG. 4A). Similar responses to cold were obtained from CHO cells transiently transfected with ANKTM1 and from Tet-inducible human embryonic kidney (HEK 293) cells stably expressing ANKTM1.).

Ruthenium red, a blocker of thermosensitive TRPV channels, also blocked cold responses by ANKTM1. Pre-incubation of ANKTM1-expressing cells in 5 µM ruthenium red followed by application of cold completely blocked responses, which were not entirely recovered after a ten minute washout (FIG. 4). Similar experiments performed with 1 µm ruthenium red caused complete block of the cold response in 90% of ANKTM1-containing cells from multiple experiments.

Icilin, an ultra-cooling agent and potent activator of TRPM8, also activated ANKTM1-expressing cells (FIG. 4B) (McKemy et al., 2002, supra), but Icilin did not activate TRPV1-expressing cells. In additional tests, capsaicin, a potent activator of TRPV1, did not activate TRPM8- or ANKTM1-expressing cells (FIG. 4B). Higher concentrations of Icilin were required for ANKTM1 activation compared to TRPM8, and the response was relatively delayed in ANKTM1 cells. There was a 15-60 second delay for ANKTM1 as compared with a 15 seconds delay for TRPM8. Therefore, it is not clear if Icilin directly binds to and activates ANKTM1.

These experiments show that both TRPM8 and ANTKM1 respond to cold. However, to confirm that threshold for activation of ANKTM1 is lower than that of TRPM8, as suggested in the above-described experimental results, further tests were conducted. The activation temperature of TRPM8 is reported at approximately 23° C. (Peier et al., 2002a, supra). Therefore, to further compare the activation temperatures of ANTKM1 and TRPM8, calcium imaging experiments were conducted wherein incubation temperature of both types of cells was elevated to 33° C. for several minutes before the bath temperature was lowered gradually to 10° C. The majority of TRPM8-expressing cells exhibited increased intracellular calcium concentration when the temperature was lowered to 20° C. (FIG. 5A). However, the majority of ANTKM1-expressing cells were not activated until the temperature was cooled to 10° C. (FIG. 5A). Quantitative analysis showed that TRPM8-expressing cells exhibited an activation threshold (defined as 20% increase from baseline fluorescence) at temperatures ranging from 19-24° C. with a mean activation temperature of 22.5±1° C. (mean±SD, n=60). By comparison, ANKTM1-expressing cells exhibited a broader range of activation temperatures (12° C.-24° C.) with an average activation temperature of 17.5±3.5° C. (mean±SD, n=100). FIG. 5B illustrates traces of typical responses of individual ANKTM1 and TRPM8-expressing cells as temperature is gradually decreased.

ANKTM1- and TRPM8-expressing CHO cells were also assayed electrophysiologically using the whole cell voltage clamp technique. The cells were clamped at −60 mV and the temperature of the perfused bath solution was decreased from 32° C. to 10° C. In ANKTM1-expressing cells small and slowly developing inward currents were observed followed by rapid and larger phase currents with an average peak amplitude of 0.55±0.07 nA (n=35) (FIGS. 6A and 6B). The activation temperature for the large evoked currents varied from cell to cell, ranging from 8-28° C., yielding results similar to those obtained by calcium imaging (n=35). A comparison of representative currents from ANKTM1- and TRPM8-expressing CHO cells shown in FIG. 6B demonstrates a lower threshold of activation for ANKTM1 than for TRPM8.

Currents evoked by decreasing the temperature in ANKTM1-expressing cells show outward rectification, but with substantial current in the inward direction (FIGS. 6C and 6D). A reversal potential of +7.7±1.2 mV was observed in an external solution containing 140 mM NaCl (n=6). Reducing the NaCl in the external solution to 40 mM (by equimolar replacement with 100 mM choline chloride) caused a negative shift in the reversal potential. This result is consistent with ANKTM1 being a cation channel. Differences in reversal potentials were used to determine the ionic selectivity of ANKTM1. The shift in reversal potential of −18 mV to −10.35±1.6 mV (n=7) seen upon replacing 100 mM NaCl with 100 mM choline Cl gives a relative permeability ratio of $P_{choline}/P_{Na}=0.28$. The reversal potentials of the cold-activated currents were similar in simplified external solutions containing 100 mM Choline and 40 mM NaCl, KCl, or CsCl. The measured reversal potentials yield relative permeability ratios of $P_K/P_{Na}=1.19$ and $P_{Cs}/P_{Na}=1.43$ (NaCl, $E_{rev}=-10.35±1.6$ mV, n=7; KCl, $E_{rev}=-7.65±1.5$ mV, n=8; CsCl, $E_{rev}=-4.75±0.75$ mV, n=7). The relative permeability of $Ca^{2+}$ and $M^{2+}$ were estimated from the shift in reversal potentials when their concentrations were raised from 1 mM to 30 mM in a 40 mM NaCl/100 mM choline Cl solution containing the divalent cation under investigation. In these tests, the reversal potential shifted from +0.54±3.3 (1 mM $CaCl_2$, n=6) to +14.16±3.9 mV (30 mM $CaCl_2$, n=6) for $Ca^{2+}$ and from −14.36±1.1 (1 mM $MgCl_2$, n=6) to +7.01±2.9 mV (30 mM $MgCl_2$, n=6) for $Mg^{2+}$, corresponding to $P_{Cs}/P_{Na}=0.84$ and $P_{Mg}/P_{Na}=1.23$ (FIG. 6D). These results indicate that ANKTM1 is a non-selective cation permeable channel, similar to many previously described TRP channels.

To investigate the properties of ANKTM1 in another heterologous system, *Xenopus* oocytes were injected with ANKTM1 cRNA. Large currents were observed in response to cold temperatures, similar to the activity of ANKTM1-expressing CHO cells (FIGS. 7A and C). In both *Xenopus* and CHO systems, a strong desensitization of ANKTM1 to cold stimuli was observed. Cold activation of ANKTM1 showed a marked desensitization during a first cold pulse, and desensitization to repeated cold pulses (FIGS. 7B and D). On average, the second cold pulse resulted in a current that was 26% of the first pulse in ANKTM1-injected oocytes (SD=6.5, n=5), compared to 78% for TRPM8 (SD=5.9, n=4).

The above-described characterization studies show that ANKTM1 belongs to the superfamily of TRP channels as does the menthol- and cold-activated receptor, TRPM8, despite the lack of amino acid sequence similarity between the two. Functional studies of ANKTM1 agree with the phylogenetic characterization of this channel as TRP-like. There is now strong evidence that a group of TRP channels play a role in temperature detection in the mammalian peripheral nervous system. ANKTM1 belongs to the third TRP subfamily shown to play a role in temperature detection. Like other thermosensitive TRPs, ANKTM1 is a non-selective cation channel. However, ANKTM1 displays several unique characteristics compared to previously characterized temperature-activated TRP channels. The variability in activation threshold temperature of ANKTM1 from cell to cell is broader when compared to other TRPs. Furthermore, the current through ANKTM1 rapidly desensitizes to cold, a property not seen to such an extent in other temperature-activated TRPs. Finally, long-term overexpression of ANKTM1 is detrimental to cells, making it necessary to for cell lines to conditionally express ANKTM1. The mechanisms underlying the threshold variability, strong desensitization, and cell toxicity are not yet clear.

ANKTM1 is activated at lower temperatures than TRPM8, starting at near 17° C., which approximates the threshold of noxious cold for humans (~15° C.). A role for ANKTM1 in noxious cold detection is also suggested by its expression pattern. Mouse ANKTM1 is specifically expressed in somatic sensory neurons. Within this population, ANKTM1 is not expressed in neurons that express TRPM8. Instead, the vast majority of ANKTM1-positive cells also express TRPV1 and CGRP, markers for pain-sensing neurons. Recent reports describe the presence of two separate populations of cold-sensitive DRG neurons: one population that expresses TRPM8 and is menthol-sensitive, and a distinct population that is menthol-insensitive and is activated at even colder temperatures. It is likely that ANKTM1 marks this second population of cold sensitive neurons.

The major overlap of ANKTM1 and TRPV1 tissue expression raises the question of how temperature/pain information is decoded in the brain and spinal cord. Electrophysiological characterization of DRG neurons has led to the labeled line hypothesis of sensory perception (Scott, 1992). According to this hypothesis, the nervous system interprets the environment by monitoring the electrical activity of distinct groups of sensory neurons that are specialized to detect a unique sensory modality. However, this hypothesis does not incorporate the observation of single neurons known to transmit more than one sensory modality, for example in this case cold and pain. Indeed, there are so-called polymodal nociceptors that respond to a variety of noxious stimuli (Julius and Basbaum, Nature 413:203-210, 2001). Here molecular evidence is shown that a cold-activated channel (ANKTM1) is expressed in a subset of heat-sensitive (TRPV1-expressing) neurons.

The identification of ANKTM1 as a channel activated by noxious cold increases the range of temperatures "sensed" by TRP channels, but does not explain how the quality of the sensation changes from pleasantly cool to aching or burning, i.e., pain, depending on whether ANKTM1, TRPM8, or both of these cold channels are active.

The term "isolated" means altered "by the hand of man" from its natural state; i.e., if it occurs in nature, it has been changed or removed from its original environment, or both. For example, a naturally occurring polynucleotide or a polypeptide naturally present in a living animal in its natural state is not "isolated", but the same polynucleotide or polypeptide separated from the coexisting materials of its natural state is "isolated", as the term is employed herein. As part of or following isolation, a polynucleotide can be joined to other polynucleotides, such as for example DNAs, for mutagenesis studies, to form fusion proteins, and for propagation or expression of the polynucleotide in a host. The isolated polynucleotides, alone or joined to other polynucleotides, such as vectors, can be introduced into host cells, in culture or in whole organisms. Such polynucleotides, when introduced into host cells in culture or in whole organisms, still would be isolated, as the term is used herein, because they would not be in their naturally occurring form or environment. Similarly, the polynucleotides and polypeptides may occur in a composition, such as a media formulation (solutions for introduction of polynucleotides or polypeptides, for example, into cells or compositions or solutions for chemical or enzymatic reactions).

"Polynucleotide" or "nucleic acid sequence" refers to a polymeric form of nucleotides. In some instances a polynucleotide refers to a sequence that is not immediately contiguous with either of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides of the invention can be ribonucleotides, deoxyribonucleotides, or modified forms of either nucleotide. In addition, the polynucleotide sequence involved in producing a polypeptide chain can include regions preceding and following the coding region (leader and trailer) as well as intervening sequences (introns) between individual coding segments (exons) depending upon the source of the polynucleotide sequence.

The term "polynucleotide(s)" generally refers to any polyribonucleotide or polydeoxyribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

In addition, the polynucleotides or nucleic acid sequences may contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein.

Nucleic acid sequences can be created which encode a fusion protein and can be operatively linked to expression control sequences. "Operatively linked" refers to a juxtaposition wherein the components so described are in a relationship permitting them to function in their intended manner. For example, a coding sequence is "operably linked" to another coding sequence when RNA polymerase will transcribe the two coding sequences into a single mRNA, which is then translated into a single polypeptide having amino acids derived from both coding sequences. The coding sequences need not be contiguous to one another so long as the expressed sequences ultimately process to produce the desired protein. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

By "promoter" is meant minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the of the polynucleotide sequence. Both constitutive and inducible promoters, are included in the invention (see e.g., Bitter et al., Methods in Enzymology 153:516-544, 1987). For example, when cloning in bacterial systems, inducible promoters such as pL of bacteriophage, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention.

A nucleic acid sequence of the invention including, for example, a polynucleotide encoding a fusion protein, may be inserted into a recombinant expression vector. A recombinant expression vector generally refers to a plasmid, virus or other vehicle known in the art that has been manipulated by insertion or incorporation of a nucleic acid sequences. For example, a recombinant expression vector of the invention includes a polynucleotide sequence encoding an ANKTM1-related polypeptide involved in nociception or a fragment thereof. The expression vector typically contains an origin of replication, a promoter, as well as specific genes that allow phenotypic selection of the transformed cells. Vectors suitable for use in the invention include, but are not limited to the T7-based expression vector for expression in bacteria (Rosenberg, et al., Gene 56:125, 1987), the pMSXND expression vector for expression in mammalian cells (Lee and Nathans, J. Biol. Chem. 263:3521, 1988), baculovirus-derived vectors for expression in insect cells, cauliflower mosaic virus, CaMV; tobacco mosaic virus, TMV. The nucleic acid sequences of the invention can also include a localization sequence to direct the indicator to particular cellular sites by fusion to appropriate organellar targeting signals or localized host proteins. For example, a polynucleotide encoding a localization sequence, or signal sequence, can be used as a repressor and thus can be ligated or fused at the 5' terminus of a polynucleotide encoding a polypeptide of the invention such that the localization or signal peptide is located at the amino terminal end of a resulting polynucleotide/polypeptide. The construction of expression vectors and the expression of genes in transfected cells involves the use of molecular cloning techniques also well known in the art. (See, for example, Sambrook et al., Molecular Cloning—A Laboratory Manual, Cold Spring Harbor Laboratory, Cold Spring Harbor, N.Y., 1989, and Current Protocols in Molecular Biology, M. Ausubel et al., eds., (Current Protocols, a joint venture between Greene Publishing Associates, Inc. and John Wiley & Sons, Inc., most recent Supplement)). These methods include in vitro recombinant DNA techniques, synthetic techniques and in vivo recombination/genetic recombination. (See also, Maniatis, et al., Molecular Cloning A Laboratory Manual, Cold Spring Harbor Laboratory, N.Y., 1989).

In yeast, a number of vectors containing constitutive or inducible promoters may be used. For a review, see Current Protocols in Molecular Biology, Vol. 2, Ed. Ausubel, et al., Greene Publish. Assoc. & Wiley Interscience, Ch. 13, 1988; Grant, et al., "Expression and Secretion Vectors for Yeast," in Methods in Enzymology, Eds. Wu & Grossman, 1987, Acad. Press, N.Y., Vol. 153, pp. 516-544, 1987; Glover, DNA Cloning, Vol. II, IRL Press, Wash., D.C., Ch. 3, 1986; and Bitter, "Heterologous Gene Expression in Yeast," Methods in Enzymology, Eds. Berger & Kimmel, Acad. Press, N.Y., Vol. 152, pp. 673-684, 1987; and The Molecular Biology of the Yeast *Saccharomyces*, Eds. Strathem et al., Cold Spring Harbor Press, Vols. I and II, 1982. A constitutive yeast promoter such as ADH or LEU2 or an inducible promoter such as GAL may be used ("Cloning in Yeast," Ch. 3, R. Rothstein In: DNA Cloning Vol. 11, A Practical Approach, Ed. D M Glover, IRL Press, Wash., D.C., 1986). Alternatively, vectors may be used which promote integration of foreign DNA sequences into the yeast chromosome.

An alternative expression system that could be used to express an invention ANKTM1-related polypeptide is an insect system. In one such system, *Autographa californica* nuclear polyhedrosis virus (AcNPV) is used as a vector to express foreign or mutated polynucleotide sequences. The virus grows in *Spodoptera frugiperda* cells. The sequence encoding an invention protein may be cloned into non-essential regions (for example, the polyhedrin gene) of the virus and placed under control of an AcNPV promoter (for example the polyhedrin promoter). Successful insertion of the sequences coding for a protein of the invention will result in inactivation of the polyhedrin gene and production of non-occluded recombinant virus (i.e., virus lacking the proteinaceous coat coded for by the polyhedrin gene). These recombinant viruses are then used to infect *S. frugiperda* cells in which the inserted gene is expressed, see Smith, et al., J. Viol. 46:584, 1983; Smith, U.S. Pat. No. 4,215,051.

The vectors of the invention can be used to transform a host cell. By transform or transformation is meant a permanent or transient genetic change induced in a cell following incorporation of new DNA (i.e., DNA exogenous to the cell). Where the cell is a mammalian cell, a permanent genetic change is generally achieved by introduction of the DNA into the genome of the cell.

A transformed cell or host cell generally refers to a cell (e.g., prokaryotic or eukaryotic) into which (or into an ancestor of which) has been introduced, by means of recombinant DNA techniques, a DNA molecule encoding an invention ANKTM1-related polypeptide or a fragment thereof.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, methods for transfection or transformation with DNA include calcium phosphate co-precipitates, conventional mechanical procedures such as microinjection, electroporation, insertion of a plasmid encased in liposomes, or virus vectors, as well as others known in the art, may be used. Eukaryotic cells can also be cotransfected with DNA sequences encoding an invention ANKTM1-related polypeptide and a second foreign DNA molecule encoding a selectable marker, such as the herpes simplex thymidine kinase gene. Another method is to use a eukaryotic viral vector, such as simian virus 40 (SV40) or bovine papilloma virus, to transiently infect or transform eukaryotic cells and express the protein. (Eukaryotic Viral Vectors, Cold Spring Harbor Laboratory, Gluzman ed., 1982). Typically, a eukaryotic host will be utilized as the host cell. The eukaryotic cell may be a yeast cell (e.g., *Saccharomyces cerevisiae*), an insect cell (e.g., *Drosophila* sp.) or may be a mammalian cell, including a human cell.

Eukaryotic systems, and mammalian expression systems, allow for post-translational modifications of expressed mammalian proteins to occur. Eukaryotic cells which possess the cellular machinery for processing of the primary transcript, glycosylation, phosphorylation, and, advantageously secretion of the gene product should be used. Such host cell lines may include, but are not limited to, CHO, VERO, BHK, HeLa, COS, MDCK, Jurkat, HEK-293, and WI38.

Mammalian cell systems that utilize recombinant viruses or viral elements to direct expression may be engineered. For example, when using adenovirus expression vectors, a polynucleotide encoding an invention ANKTM1-related polypeptide may be ligated to an adenovirus transcription/translation control complex, e.g., the late promoter and tripartite leader sequence. This chimeric sequence may then be inserted in the adenovirus genome by in vitro or in vivo recombination. Insertion in a non-essential region of the viral genome (e.g., region E1 or E3) will result in a recombinant virus that is viable and capable of expressing an invention ANKTM1-related polypeptide or a fragment thereof in infected hosts (e.g., see Logan & Shenk, Proc. Natl. Acad. Sci. USA, 81:3655-3659, 1984). Alternatively, the vaccinia virus 7.5K promoter may be used. (e.g., see, Mackett, et al., Proc. Natl. Acad. Sci. USA, 79:7415-7419, 1982; Mackett, et al., J. Virol. 49:857-864, 1984; Panicali, et al., Proc. Natl. Acad. Sci. USA 79:4927-4931, 1982). Of particular interest are vectors based on bovine papilloma virus, which have the ability to replicate as extrachromosomal elements (Sarver, et al., Mol. Cell. Biol. 1:486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of an invention nociception-related gene in host cells (Cone & Mulligan, Proc. Natl. Acad. Sci. USA, 81:6349-6353, 1984). High-level expression may also be achieved using inducible promoters, including, but not limited to, the metallothionein IIA promoter and heat shock promoters.

For long-term, high-yield production of recombinant proteins, stable expression is preferred. Rather than using expression vectors that contain viral origins of replication, host cells can be transformed with the cDNA encoding an invention ANKTM1-related polypeptide controlled by appropriate expression control elements (e.g., promoter, enhancer, sequences, transcription terminators, polyadenylation sites, etc.), and a selectable marker. The selectable marker in the recombinant vector confers resistance to the selection and allows cells to stably integrate the plasmid into their chromosomes and grow to form foci, which in turn can be cloned and expanded into cell lines. For example, following the introduction of foreign DNA, engineered cells may be allowed to grow for 1-2 days in an enriched media, and then are switched to a selective media. A number of selection systems may be used, including, but not limited to, the herpes simplex virus thymidine kinase (Wigler, et al., Cell, 11:223, 1977), hypoxanthine-guanine phosphoribosyltransferase (Szybalska & Szybalski, Proc. Natl. Acad. Sci. USA, 48:2026, 1962), and adenine phosphoribosyltransferase (Lowy, et al., Cell, 22:817, 1980) genes can be employed in tk–, hgprt– or aprt– cells respectively. Also, anti-metabolite resistance can be used as the basis of selection for dhfr, which confers resistance to methotrexate (Wigler, et al., Proc. Natl. Acad. Sci. USA, 77:3567, 1980; O'Hare, et al., Proc. Natl. Acad. Sci. USA, 8:1527, 1981); gpt, which confers resistance to mycophenolic acid (Mulligan & Berg, Proc. Natl. Acad. Sci. USA, 78:2072, 1981; neo, which confers resistance to the aminoglycoside G-418 (Colberre-Garapin, et al., J. Mol. Biol. 150:1, 1981); and hygro, which confers resistance to hygromycin (Santerre, et al., Gene 30:147, 1984) genes. Recently, additional selectable genes have been described, namely trpB, which allows cells to utilize indole in place of tryptophan; hisD, which allows cells to utilize histinol in place of histidine (Hartman & Mulligan, Proc. Natl. Acad. Sci. USA 85:8047, 1988); and ODC (ornithine decarboxylase) which confers resistance to the ornithine decarboxylase inhibitor, 2-(difluoromethyl)-DL-ornithine, DFMO (McConlogue L., In: Current Communications in Molecular Biology, Cold Spring Harbor Laboratory, ed., 1987).

The term "primer" as used herein refers to an oligonucleotide, whether natural or synthetic, which is capable of acting as a point of initiation of synthesis when placed under conditions in which primer extension is initiated or possible. Synthesis of a primer extension product that is complementary to a nucleic acid strand is initiated in the presence of nucleoside triphosphates and a polymerase in an appropriate buffer at a suitable temperature. For instance, if a nucleic acid sequence is inferred from a protein sequence, a primer generated to synthesize nucleic acid sequence encoding the protein sequence is actually a collection of primer oligonucleotides containing sequences representing all possible codon variations based on the degeneracy of the genetic code. One or more of the primers in this collection will be homologous with the end of the target sequence. Likewise, if a "conserved" region shows significant levels of polymorphism in a population, mixtures of primers can be prepared that will amplify adjacent sequences.

A polypeptide or protein refers to a polymer in which the monomers are amino acid residues that are joined together through amide bonds. When the amino acids are alpha-amino acids, either the L-optical isomer or the D-optical isomer can be used, the L-isomers being typical. An invention ANKTM1-related polypeptide is intended to encompass any amino acid sequence and include modified sequences such as glycoproteins, which provides a polypeptide having nociception modulating activity. Accordingly, the polypeptides of the invention are intended to cover naturally occurring proteins, as well as those that are recombinantly or synthetically synthesized. In addition, an invention ANKTM1-related polypeptide can occur in at least two different conformations wherein both conformations have the same or substantially the same amino acid sequence but have different three-dimensional structures so long as they have a biological activity related to nociception. Polypeptide or protein fragments are also encompassed by the invention. Fragments can have the same or substantially the same amino acid sequence as the naturally occurring protein. A polypeptide or peptide having substantially the same sequence means that an amino acid sequence is largely, but not entirely, the same, but retains a functional activity of the sequence to which it is related. In general polypeptides of the invention include peptides, or full-length protein, that contains substitutions, deletions, or insertions into the protein backbone, that would still have an approximately 70%-90% homology to the original protein over the corresponding portion. A yet greater degree of departure from homology is allowed if like-amino acids, i.e. conservative amino acid substitutions, do not count as a change in the sequence A polypeptide may be substantially related but for a conservative variation, such polypeptides being encompassed by the invention. A conservative variation denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. Other illustrative examples of conservative substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; thieonine to serine; tryptophan to tyrosine; tyrosine to tryptophan or phenylalanine; valine to isoleucine to leucine. The term "conservative variation" also includes the use of a substituted amino acid in place of an unsubstituted parent amino acid provided that antibodies raised to the substituted polypeptide also immunoreact with the unsubstituted polypeptide.

Modifications and substitutions are not limited to replacement of amino acids. For a variety of purposes, such as increased stability, solubility, or configuration concerns, one skilled in the art will recognize the need to introduce, (by deletion, replacement, or addition) other modifications. Examples of such other modifications include incorporation of rare amino acids, dextra-amino acids, glycosylation sites, cytosine for specific disulfide bridge formation. The modified peptides can be chemically synthesized, or the isolated gene can be site-directed mutagenized, or a synthetic gene can be synthesized and expressed in bacteria, yeast, baculovirus, tissue culture and so on.

In one embodiment, the invention provides an isolated polynucleotide sequence encoding an invention ANKTM1-related polypeptide. An invention ANKTM1-related polypeptide can be characterized by its ability to modulate nociceptive responses. Polynucleotide sequences of the invention include DNA, cDNA and RNA sequences that encode a nociceptive-related polypeptide of the invention as well as complementary sequences thereof. It is understood that all polynucleotides encoding all or a portion of an invention ANKTM1-related polypeptide are also included herein, so long as they encode a polypeptide with nociceptive activity (e.g., modulation of nociceptive responses). Such polynucleotides include naturally occurring, synthetic, and intentionally manipulated polynucleotides. For example, a nociceptive polynucleotide of the invention may be subjected to site-directed mutagenesis. The polynucleotides of the invention include sequences that are degenerate as a result of the genetic code. There are 20 natural amino acids, most of which are specified by more than one codon. Therefore, all degenerate nucleotide sequences are included in the invention so long as the amino acid sequence of an invention ANKTM1-related polypeptide encoded by the nucleotide sequence is functionally unchanged. In addition, polypeptide fragments of an invention ANKTM1-related polypeptide, and their corresponding polynucleotide sequences are encompassed by the current invention, so long as the polypeptides retain some biological activity related to nociception. A biological activity related to nociception includes for example, antigenicity or the ability to modulate nociceptive responses. Assays described in the examples below are capable of identifying such fragments or modified polypeptides having a biological activity related to nociception. For example, a polypeptide that modulates a nociceptive response (e.g., intracellular calcium imaging tests) is encompassed by the invention whether it is expressed in vivo by the organism or administered to the organism.

The polynucleotides and polypeptides of this invention were originally recovered from human and mouse tissue. Thus, the present invention provides means for isolating the nucleic acid molecules from other organisms, encoding the invention ANKTM1-related polypeptides. For example, one may probe a gene library with a natural or artificially designed probe using art recognized procedures (see, for example: Current Protocols in Molecular Biology, Ausubel F. M. et al. (Eds.) Green Publishing Company Assoc. and John Wiley Interscience, New York, 1989, 1992). It is appreciated by those skilled in the art that probes can be designed based on the degeneracy of the genetic code to a sequences corresponding to a polypeptide or polynucleotide of the invention.

In addition, sequencing algorithms can be used to measure homology or identity between known and unknown sequences. Such methods and algorithms are useful in identifying corresponding sequences present in other organisms. Homology or identity is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various deletions, substitutions and other modifications. The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

Methods for alignment of sequence for comparison are well known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method for Person & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

On example of a useful algorithm is BLAST and BLAST 2.0 algorithms, which are described in Altschul et al., Nuc. Acids Res. 25:3389-3402 (1977) and Altschul et al., J. Mol. Biol. 215:403-410 (1990), respectively. Software for performing BLAST analyses is publicly available through the National Center for Biotechnology Information. The BLAST algorithm also performs a statistical analysis of the similarity between two sequences (see, e.g., Karlin & Altschul, Proc. Natl. Acad. Sci. USA 90:5873 (1993)). Other algorithms for determining homology or identity are well known in the art. Such alignment programs can also be used to screen genome databases to identify polynucleotide sequences having substantially identical sequences.

A "substantially pure polypeptide" is typically pure when it is at least 60%, by weight, free from the proteins and naturally occurring organic molecules with which it is naturally associated. Preferably, the preparation is at least 75%, more preferably at least 90%, and most preferably at least 99%, by weight, an invention ANKTM1-related polypeptide. A substantially pure ANKTM1-related polypeptide may be obtained, for example, by extraction from a natural source (e.g., a mammalian cell); by expression of a recombinant nucleic acid encoding an ANKTM1-related polypeptide; or by chemically synthesizing the protein. Purity can be measured by any appropriate method, e.g., by column chromatography, polyacrylamide gel electrophoresis, or by HPLC analysis.

In addition to polypeptides of the invention, specifically disclosed herein is a DNA sequence for an invention ANKTM1-related polypeptide. DNA sequences of the invention can be obtained by several methods. For example, the DNA can be isolated using hybridization or computer-based techniques that are well known in the art. These include, but are not limited to: 1) hybridization of genomic libraries with probes to detect homologous nucleotide sequences; 2) antibody screening of expression libraries to detect cloned DNA fragments with shared structural features; 3) polymerase chain reaction (PCR) on genomic DNA using primers capable of annealing to the DNA sequence of interest; and 4) computer searches of sequence databases for similar sequences as described above.

The polynucleotide encoding an invention ANKTM1-related polypeptide includes complementary polynucleotide sequences, as well as splice variants thereof. When the sequence is RNA, the deoxyribonucleotides A, G, C, and T are replaced by ribonucleotides A, G, C, and U, respectively. Also included in the invention are fragments (portions) of the above-described nucleic acid sequences that are at least 15 bases in length, which is sufficient to permit the fragment to selectively hybridize to DNA that encodes a polypeptide sequence of the invention. "Selective hybridization" as used herein refers to hybridization under moderately stringent or highly stringent physiological conditions (See, for example, the techniques described in Maniatis et al., 1989 Molecular Cloning A Laboratory Manual, Cold Spring Harbor Laboratory, N.Y., incorporated herein by reference), which distinguishes related from unrelated nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

Oligonucleotides encompassed by the present invention are also useful as primers for nucleic acid amplification reactions. In general, the primers used according to the method for the invention embrace oligonucleotides of sufficient length and appropriate sequence to provide specific initiation of polymerization of a significant number of nucleic acid molecules containing the target nucleic acid under the conditions of stringency for the reaction utilizing the primers. In this manner, it is possible to selectively amplify the specific target nucleic acid sequence containing the nucleic acid of interest.

Amplified products may be detected by Southern blot analysis, without using radioactive probes. In such a process, for example, a small sample of DNA containing a very low level of a nucleotide sequence is amplified and analyzed via a Southern blotting technique known to those of skill in the art. The use of non-radioactive probes or labels is facilitated by the high level of the amplified signal.

Screening procedures that rely on nucleic acid hybridization make it possible to isolate any gene sequence from any organism, provided the appropriate probe is available. For example, it is envisioned that such probes can be used to identify other homologs of the ANKTM1-related polynucleotide family of factors in mammals or, alternatively, in other organisms such as invertebrates. In accomplishing this, alignment algorithms (as described above) can be used to screen genome databases. Alternatively, oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of DNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., Nucl. Acid Res., 9:879, 1981).

When the entire sequence of amino acid residues of the desired polypeptide is not known, the direct synthesis of DNA sequences is not possible and the method for choice is use of cDNA sequences. Among the standard procedures for isolating cDNA sequences of interest is the formation of plasmid- or phage-carrying cDNA libraries, which are derived from reverse transcription of mRNA, which is abundant in donor cells that have a high level of genetic expression. When used in combination with polymerase chain reaction technology, even rare expression products can be cloned.

DNA sequences encoding an invention ANKTM1-related polypeptide can be expressed in vitro by DNA transfer into a suitable host cell, as described above.

The invention ANKTM1-related polynucleotide sequences may be inserted into a recombinant expression vector. The term "recombinant expression vector" refers to a plasmid, virus or other vehicle known in the art that has been manipulated by insertion or incorporation of the nociception-related genetic sequences. Such expression vectors contain a promoter sequence that facilitates the efficient transcription of the inserted genetic sequence of the host. The expression vector typically contains an origin of replication, a promoter, as well as specific genes that allow phenotypic selection of the transformed cells. Vectors suitable for use in the present invention include those described above.

Polynucleotide sequences encoding a nociception-related polypeptide can be expressed in either prokaryotes or eukaryotes. Hosts can include microbial, yeast, insect and mammalian organisms. Such vectors are used to incorporate DNA sequences of the invention.

Methods that are well known to those skilled in the art can be used to construct expression vectors containing the ANKTM1-related polypeptide coding sequence and appropriate transcriptional/translational control signals. These methods include in vitro recombinant DNA techniques, synthetic techniques, and in vivo recombination/genetic techniques. (See, for example, the techniques described in Maniatis et al., 1989, Molecular Cloning A Laboratory Manual, Cold Spring Harbor Laboratory, N.Y.).

The genetic construct can be designed to provide additional benefits, such as, for example addition of C-terminal or N-terminal amino acid residues that would facilitate purification by trapping on columns or by use of antibodies. All those methodologies are cumulative. For example, a synthetic gene can later be mutagenized. The choice as to the method for producing a particular construct can easily be made by one skilled in the art based on practical considerations: size of the desired peptide, availability and cost of starting materials, etc. All the technologies involved are well established and well known in the art. See, for example, Ausubel et al., Current Protocols in Molecular Biology, Volumes 1 and 2 (1987), with supplements, and Maniatis et al., Molecular Cloning, a Laboratory Manual, Cold Spring Harbor Laboratory (1989). Yet other technical references are known and easily accessible to one skilled in the art.

In another embodiment, the invention provides antibodies that bind to an invention ANKTM1-related polypeptide. Such antibodies are useful for research and diagnostics in the study of pain, nociceptive responses, central nervous system regulation and modulation of pain, and nociceptive-associated pathologies in general. For example, the invention allows for the diagnosis in a subject of hyperalgesia associated with improper nociceptive pain regulation. Preferably the subject is a human.

Such antibodies may be administered alone or contained in a pharmaceutical composition comprising antibodies against an invention ANKTM1-related polypeptide and other reagents effective as modulators of nociceptive pain and associated pain disorders both in vitro and in vivo.

The term "epitope", as used herein, refers to an antigenic determinant on an antigen, such as an invention ANKTM1-related polypeptide, to which the paratope of an antibody, such as an antibody that binds to an invention ANKTM1-related polypeptide. Antigenic determinants usually consist of chemically active surface groupings of molecules, such as amino acids or sugar side chains, and can have specific three-dimensional structural characteristics, as well as specific charge characteristics.

Antibodies that bind to a polypeptide of the invention can be prepared using an intact polypeptide or fragments containing small peptides of interest as the immunizing antigen. The polypeptide or a peptide used to immunize an animal can be derived from translated cDNA or chemical synthesis, which can be conjugated to a carrier protein, if desired. Such commonly used carriers, which are chemically coupled to the peptide, include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, Current Protocols in Immunology, Wiley Interscience, 1991, incorporated by reference).

It is also possible to use the anti-idiotype technology to produce monoclonal antibodies that mimic an epitope. For example, an anti-idiotypic monoclonal antibody made to a first monoclonal antibody will have a binding domain in the hypervariable region that is the "image" of the epitope bound by the first monoclonal antibody.

Antibodies of the invention include polyclonal antibodies, monoclonal antibodies, and fragments of polyclonal and monoclonal antibodies.

The preparation of polyclonal antibodies is well known to those skilled in the art. See, for example, Green et al., Production of Polyclonal Antisera, in Immunochemical Protocols (Manson, ed.), pages 1-5 (Humana Press 1992); Coligan et al., Production of Polyclonal Antisera in Rabbits, Rats, Mice and Hamsters, in Current Protocols in Immunology, section 2.4.1 (1992), which are hereby incorporated by reference.

The preparation of monoclonal antibodies likewise is conventional. See, for example, Kohler & Milstein, Nature, 256: 495 (1975); Coligan et al., sections 2.5.1-2.6.7; and Harlow et al., Antibodies: A Laboratory Manual, page 726 (Cold Spring Harbor Pub. 1988), which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1-2.7.12 and sections 2.9.1-2.9.3; Barnes et al., Purification of Immunoglobulin G (IgG), in Methods in Molecular Biology, Vol. 10, pages 79-104 (Humana Press 1992). Methods for in vitro and in vivo multiplication of monoclonal antibodies is well known to those skilled in the art. Multiplication in vitro may be carried out in suitable culture media such as Dulbecco's Modified Eagle Medium or RPMI 1640 medium, optionally replenished by a mammalian serum such as fetal calf serum or trace elements and growth-sustaining supplements such as normal mouse peritoneal exudate cells, spleen cells, bone marrow macrophages. Production in vitro provides relatively pure antibody preparations and allows scale-up to yield large amounts of the desired antibodies. Large-scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., osyngeneic mice, to cause growth of antibody-producing tumors. Optionally, the animals are primed with a hydrocarbon, especially oils such as pristane tetramethylpentadecane prior to injection. After one to three weeks, the desired monoclonal antibody is recovered from the body fluid of the animal.

Therapeutic applications for antibodies disclosed herein are also part of the present invention. For example, antibodies of the present invention may also be derived from subhuman primate antibody. General techniques for raising therapeutically useful antibodies in baboons can be found, for example, in Goldenberg et al., International Patent Publication WO 91/11465 (1991) and Losman et al., Int. J. Cancer, 46:310 (1990), which are hereby incorporated by reference.

Alternatively, an anti-ANKTM1-related polypeptide antibody may be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., Proc. Nat'l Acad. Sci. USA, 86:3833 (1989), which is hereby incorporated in its entirety by reference. Techniques for producing humanized monoclonal antibodies are described, for example, by Jones et al., Nature, 321:522 (1986); Riechmann et al., Nature, 332:323 (1988); Verhoeyen et al., Science, 239:1534 (1988); Carter et al., Proc. Nat'l Acad. Sci. USA, 89:4285 (1992); Sandhu, Crit. Rev. Biotech., 12:437 (1992); and Singer et al., J. Immunol., 150:2844 (1993), which are hereby incorporated by reference.

Antibodies of the invention also may be derived from human antibody fragments isolated from a combinatorial immunoglobulin library. See, for example, Barbas et al., Methods: A Companion to Methods in Enzymology, Vol. 2, page 119 (1991); Winter et al., Ann. Rev. Immunol. 12:433 (1994), which are hereby incorporated by reference. Cloning and expression vectors that are useful for producing a human immunoglobulin phage library can be obtained, for example, from Stratagene Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet., 7:13 (1994); Lonberg et al., Nature, 368:856 (1994); and Taylor et al., Int. Immunol., 6:579 (1994), which are hereby incorporated by reference.

Antibody fragments of the invention can be prepared by proteolytic hydrolysis of the antibody or by expression in E. coli of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg in U.S. Pat. Nos. 4,036,945 and 4,331,647, and references contained therein. These patents are hereby incorporated in their entireties by reference. See also Nisonhoff et al., Arch. Biochem. Biophys,. 89:230 (1960); Porter, Biochem. J., 73:119 (1959); Edelman et al., Methods in Enzymology, Vol. 1, page 422 (Academic Press 1967); and Coligan et al. at sections 2.8.1-2.8.10 and 2.10.1-2.10.4.

Other methods for cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent, as described in Inbar et al., Proc. Nat'l Acad. Sci. USA, 69:2659 (1972). Alternatively, the variable chains can be linked by an intermolecular disulfide bond or cross-linked by chemicals such as glutaraldehyde. See, e.g., Sandhu, supra. Preferably, the $F_v$ fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow et al., Methods: A Companion to Methods in Enzymology, Vol. 2, page 97 (1991); Bird et al., Science, 242:423 (1988); Ladner et al., U.S. Pat. No. 4,946,778; Pack et al., Bio/Technology, 11:1271 (1993); and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., Methods: A Companion to Methods in Enzymology, Vol. 2, page 106 (1991).

In one embodiment, the invention provides a method for modulating (e.g., inhibiting) nociceptive pain in a subject by administering to a cell or subject an effective amount of a composition which contains an invention ANKTM1-related polypeptide, or biologically functional fragment thereof, or an agent (e.g, an antibody, ribozyme, antisense molecule, or double-stranded interfering RNA molecules) that interacts with or inhibits expression of an invention ANKTM1-related polypeptide.

As used herein, an "effective amount" of a composition containing ANKTM1-related polypeptide or an invention ANKTM1-related polypeptide-modulating agent is defined as that amount that is effective in modulating nociceptive pain or a nociceptive response in a subject. For example, an inhibitory-effective amount would be that amount of the composition or agent sufficient to inhibit a nociceptive pain response. One skilled in the art can easily identify agents that modulate as well as the effective amount of an agent that modulates nociceptive response by using, for example, the intracellular calcium imaging tests described in the Examples herein and others as are known in the art. Briefly, a determination can be made as to the effectiveness or effective concentration or amount of an agent by contacting a cell expressing an invention ANKTM1-related polypeptide, such as mANKTM1 or hANKTM1 with the test agent or concentration and then exposing the cell to a noxious agent (e.g., a temperature of about 10-15° C.) and determining the cell's response (e.g., using electrophysiological studies or intracellular calcium imaging techniques as described herein) in the presence and absence of the agent.

In another embodiment, the present invention provides a method for modulating expression of an invention ANKTM1-related polypeptide as well as methods for screening for agents that modulate ANKTM1-related polypeptide gene expression. In this embodiment, a cell or subject is contacted with an agent suspected or known to have ANKTM1-related polypeptide expression modulating activity. The change in ANKTM1-related polypeptide gene expression is then measured as compared to a control or standard sample. The control or standard sample can be the baseline expression of the cell or subject prior to contact with the agent. An agent that modulates ANKTM1-related polypeptide gene expression may be a polynucleotide, for example, the polynucleotide may be an antisense, a triplex agent, a ribozyme, or a double-stranded interfering RNA. For example, an antisense molecule may be directed to the structural gene region or to the promoter region of ANKTM1-related polypeptide gene. The agent may be an agonist, antagonist, peptide, peptidomimetic, antibody, or chemical.

Double-stranded interfering RNA molecules are especially useful to inhibit expression of a target gene. For example, double-stranded RNA molecules can be injected into a target cell or organism to inhibit expression of a gene and the resultant gene products activity. It has been found that such double-stranded RNA molecules are more effective at inhibiting expression than either RNA strand alone. (Fire et al., Nature, 1998, 19:391(6669):806-11).

When a disorder is associated with abnormal expression of an invention ANKTM1-related polypeptide (e.g., overexpression, or expression of a mutated form of the protein), a therapeutic approach that directly interferes with the translation of an invention ANKTM1-related polypeptide is possible. Alternatively, similar methodology may be used to study gene activity. For example, antisense nucleic acid, double-stranded interfering RNA or ribozymes could be used to bind to the invention ANKTM1-related polypeptide mRNA sequence or to cleave it. Antisense RNA or DNA molecules bind specifically with a targeted gene's RNA message, interrupting the expression of that gene's protein product. The antisense binds to the messenger RNA forming a double stranded molecule that cannot be translated by the cell. Antisense oligonucleotides of about 15-25 nucleotides are preferred since they are easily synthesized and have an inhibitory effect just like antisense RNA molecules. In addition, chemically reactive groups, such as iron-linked ethylenediaminetetraacetic acid (EDTA-Fe) can be attached to an antisense oligonucleotide, causing cleavage of the RNA at the site of hybridization. Antisense nucleic acids are DNA or RNA molecules that are complementary to at least a portion of a specific mRNA molecule (Weintraub, Scientific American, 262:40, 1990). In the cell, the antisense nucleic acids hybridize to the corresponding mRNA, forming a double-stranded molecule. The antisense nucleic acids interfere with the translation of the mRNA, since the cell will not translate an mRNA that is double-stranded. Antisense oligomers of about 15 nucleotides are preferred, since they are easily synthesized and are less likely to cause problems than larger molecules when introduced into the target ANKTM1-related polypeptide-producing cell. The use of antisense methods to inhibit the in vitro translation of genes is well known in the art (Marcus-Sakura, Anal. Biochem., 172:289, 1988).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., Antisense Res. and Dev., 1:227, 1991; Helene, Anticancer Drug Design, 6:569, 1991).

Ribozymes are RNA molecules possessing the ability to specifically cleave other single-stranded RNA in a manner analogous to DNA restriction endonucleases. Through the modification of nucleotide sequences that encode these RNAs, it is possible to engineer molecules that recognize specific nucleotide sequences in an RNA molecule and cleave it (Cech, J. Amer. Med. Assn., 260:3030, 1988). A major advantage of this approach is that, because they are sequence-specific, only mRNAs with particular sequences are inactivated.

There are two basic types of ribozymes namely, tetrahymena-type (Hasselhoff, Nature, 334:585, 1988) and "hammerhead"-type. Tetrahymena-type ribozymes recognize sequences that are four bases in length, while "hammerhead"-type ribozymes recognize base sequences 11-18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-base recognition sequences are preferable to shorter recognition sequences.

These and other uses of antisense and ribozymes methods to inhibit the in vivo translation of genes are known in the art (e.g., De Mesmaeker, et al., Curr. Opin. Struct. Biol., 5:343, 1995; Gewirtz, A. M., et al., Proc. Natl. Acad. Sci. U.S.A., 93:3161, 1996b; Stein, C. A., Chem. and Biol. 3:319, 1996).

Delivery of antisense, triplex agents, ribozymes, competitive inhibitors, double-stranded interfering RNA and the like can be achieved using a recombinant expression vector such as a chimeric virus or a colloidal dispersion system or by injection. Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a polynucleotide sequence of interest into the viral vector, along with another gene that encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the antisense polynucleotide.

Another targeted delivery system for polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles that are useful as delivery vehicles in vitro and in vivo. It has been shown that large unilamellar vesicles (LUV), which range in size from 0.2-4.0 µm can encapsulate a substantial percentage of an aqueous buffer containing large macromolecules. RNA, DNA and intact virions can be encapsulated within the aqueous interior and be delivered to cells in a biologically active form (Fraley, et al., Trends Biochem. Sci., 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., Biotechniques, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidyl-glycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

The targeting of liposomes has been classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs that contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. In general, the compounds bound to the surface of the targeted delivery system will be ligands and receptors which will allow the targeted delivery system to find and "home in" on the desired cells. A ligand may be any compound of interest that will bind to another compound, such as a receptor.

The agents useful in the method for the invention can be administered, for in vivo application, parenterally by injection or by gradual perfusion over time. Administration may be intravenously, intraperitoneally, intramuscularly, subcutaneously, intracavity, or transdermally. For in vitro studies the agents may be added or dissolved in an appropriate biologically acceptable buffer and added to a cell or tissue.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents and inert gases and the like.

It is envisioned that the invention can be used to treat pathologies associated with hyperalgesia and nociceptive pain associated disorders. Therefore, the present invention encompasses methods for ameliorating a disorder associated with nociception, including treating a subject having the disorder, at the site of the disorder, with an agent which modulates an invention ANKTM1-related polypeptide. Generally, the terms "treating", "treatment" and the like are used herein to mean affecting a subject, tissue or cell to obtain a desired pharmacologic and/or physiologic effect. The effect may be prophylactic in terms of completely or partially preventing a disease or sign or symptom thereof, and/or may be therapeutic in terms of a partial or complete cure for hyperalgesia and nociceptive pain associated disorders and/or adverse effect, such as pain, attributable to the hyperalgesia and nociceptive pain associated disorders. "Treating" as used herein covers any treatment of, or prevention of hyperalgesia and nociceptive pain associated disorders in an invertebrate, a vertebrate, a mammal, particularly a human, and includes: (a) preventing the disorder from occurring in a subject that may be predisposed to the disorder, but has not yet been diagnosed as having it; (b) inhibiting the disorder, i.e., arresting its development; or (c) relieving or ameliorating the disorder cause regression of one or more symptoms of the hyperalgesia and/or nociceptive pain associated disorder.

The invention includes various pharmaceutical compositions useful for ameliorating symptoms attributable to a nociceptive pain-associated disorder. The pharmaceutical compositions according to the invention are prepared by bringing an antibody against ANKTM1-related polypeptide, a polypeptide or peptide derivative of an invention ANKTM1-related polypeptide, an invention ANKTM1-related polypeptide mimetic, a drug, chemical or combination of chemicals or an invention ANKTM1-related polypeptide-modulating agent into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 15th ed. Easton: Mack Publishing Co., 1405-1412, 1461-1487 (1975) and The National Formulary XIV., 14th ed. Washington: American Pharmaceutical Association (1975), the contents of which are hereby incorporated by reference. The pH and exact concentration of the various components of the pharmaceutical composition are adjusted according to routine skills in the art. See Goodman and Gilman's The Pharmacological Basis for Therapeutics (7th ed.).

The pharmaceutical compositions are preferably prepared and administered in dose units. Solid dose units are tablets, capsules and suppositories. For treatment of a subject, depending on activity of the compound, manner of administration, nature and severity of the disorder, age and body weight of the subject, different daily doses are necessary. Under certain circumstances, however, higher or lower daily doses may be appropriate. The administration of the daily dose can be carried out both by single administration in the form of an individual dose unit or else several smaller dose units and also by multiple administrations of subdivided doses at specific intervals.

The pharmaceutical compositions according to the invention may be administered locally or systemically in a therapeutically effective dose. Amounts effective for this use will, of course, depend on the severity of the disease and the weight and general state of the subject. Typically, dosages used in vitro may provide useful guidance in the amounts useful for in situ administration of the pharmaceutical composition, and animal models may be used to determine effective dosages for treatment of particular disorders. Various considerations are described, e.g., in Langer, Science, 249:1527, (1990); Gilman et al. (eds.) (1990), each of which is herein incorporated by reference.

In one embodiment, the invention provides a pharmaceutical composition useful for administering an invention ANKTM1-related polypeptide, or nucleic acid encoding an invention ANKTM1-related polypeptide, to a subject in need of such treatment. "Administering" the pharmaceutical composition of the present invention may be accomplished by any means known to the skilled artisan. Preferably a "subject" refers to a mammal, most preferably a human, but may be any organism.

An invention ANKTM1-related polypeptide or antibody can be administered parenterally, enterically, by injection, rapid infusion, nasopharyngeal absorption, dermal absorption, rectally and orally. Pharmaceutically acceptable carrier preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers for occlusive dressings can be used to increase skin permeability and enhance antigen absorption. Liquid dosage forms for oral administration may generally comprise a liposome solution containing the liquid dosage form. Suitable solid or liquid pharmaceutical preparation forms are, for example, granules, powders, tablets, coated tablets, (micro)capsules, suppositories, syrups, emulsions, suspensions, creams, aerosols, drops or injectable solution in ampule form and also preparations with protracted release of active compounds, in whose preparation excipients and additives and/or auxiliaries such as disintegrants, binders, coating agents, swelling agents, lubricants, flavorings, sweeteners and elixirs containing inert diluents commonly used in the art, such as purified water.

In another embodiment, the invention provides a method for identifying a agent which modulates ANKTM1-related polypeptide expression or activity including incubating components comprising the agent and an invention ANKTM1-related polypeptide, or a recombinant cell expressing an invention ANKTM1-related polypeptide, under conditions sufficient to allow the agent to interact and determining the affect of the agent on the expression or activity of the gene or polypeptide, respectively. The term "affect", as used herein, encompasses any means by which gene expression or protein activity can be modulated. Such agents can include, for example, polypeptides, peptidomimetics, chemical compounds, small molecules and biologic agents as described below.

Incubating includes conditions that allow contact between the test agent and an invention ANKTM1-related polypeptide, a cell expressing an invention ANKTM1-related polypeptide or nucleic acid encoding an invention ANKTM1-related polypeptide. Contacting includes in solution and in solid phase. The test agent may optionally be a combinatorial library for screening a plurality of agents. Agents identified in the method for the invention can be further evaluated, detected, cloned, sequenced, and the like, either in solution or after binding to a solid support, by any method usually applied to the detection of a specific DNA sequence such as PCR, oligomer restriction (Saiki, et al., Bio/Technology, 3:1008-1012, 1985), oligonucleotide ligation assays (OLAs) (Landegren, et al., Science, 241:1077, 1988), and the like. Molecular techniques for DNA analysis have been reviewed (Landegren, et al., Science, 242:229-237, 1988).

Thus, the method for the invention includes combinatorial chemistry methods for identifying chemical agents that bind to or affect ANKTM1-related polypeptide expression or activity.

Areas of investigation are the development of therapeutic treatments. The screening identifies agents that provide modulation of ANKTM1-related polypeptide function in targeted organisms. Of particular interest are screening assays for agents that have a low toxicity or a reduced number of side effects for humans.

The term "agent" as used herein describes any molecule, e.g. protein or pharmaceutical, with the capability of altering or mimicking the physiological function or expression of an invention ANKTM1-related polypeptide. Generally, a plurality of assay mixtures is run in parallel with different agent concentrations to obtain a differential response to the various concentrations. Typically, one of these concentrations serves as a negative control, i.e. at zero concentration or below the level of detection.

As used herein, an agent that acts, directly or indirectly via a receptor or receptors responsible for mediating or involved in peripheral hyperalgesia, by antagonizing the activity of hyperalgesia mediating agents, such as a prostaglandin, is an agent intended for use herein, if it also does not exhibit CNS effects as defined herein. Such agent is a peripheral antihyperalgesic. The activity of antihyperalgesic agents is distinct from the activity of centrally acting analgesic agents (e.g., agents that act by virtue of crossing the blood brain barrier). Anti-hyperalgesic agents act to block hypersensitivity. The compositions and methods for the invention are intended for prevention and/or the amelioration of the symptoms of hyperalgesia by decreasing or eliminating the hyperalgesia or by preventing its onset. An antihyperalgesic agent is distinct from a local anesthetic, which is an agent that produces numbness by abolishing sensitivity to touch, and other stimuli, including pain stimuli. Local anesthetics abolish sensation, including pain, by blocking conduction in nerve axons in the peripheral nervous system. Antihyperalgesics, on the other hand, alleviate pain by elevating a patient's threshold to pain. Thus, unlike anesthetics, antihyperalgesics reduce sensation to pain during states of increased sensitivity (e.g., hyperalgesia) without substantially affecting normal sensitivity to touch and/or other stimuli.

Antihyperalgesics are agents that may reduce hypersensitivity to touch and other stimuli that would not, under normal circumstances, evoke a pain response. The hyperalgesic response is an exaggerated response, such as excessive sensitiveness or sensibility to pain from touch, slight exertion, warmth and the like. Antihyperalgesics may be identified, for example, by the Randall-Selitto method (see, e.g., Randall et al. Arch. Int. Pharmacodyn. 111:409-419, 1957), as well as the formalin, carrageenan and yeast induced inflammation methods. In addition to the antihyperalgesic effect, the antihyperalgesic agents provided herein may concurrently provide an analgesic effect.

Analgesics are agents that may reduce a patient's perception of pain evoked by stimuli that are acutely painful under normal circumstances. Thus, analgesics may be effective in reducing the acute and immediate pain associated with trauma (e.g., pinpricks, burns, or crushing wounds) as well as chronic pain, that is not normally associated with peripheral sensitization, such as cancer or headache pain.

In addition, cells or organisms which have a mutation in an invention ANKTM1-related polypeptide sequence may be used as models to screen for agents which modulate disorders associated with the mutation. For example, if organisms are identified that lack normal nociceptive response activity due to a mutation in an invention nociception-related polypeptide sequence, administration of agents to an organism having such a mutation, or cells derived or recombinantly modified to have a reduced nociceptive activity, may be used to determine the effect of the drug or agent on nociception.

In a further embodiment, the invention provides a method for detecting ANKTM1-related polypeptide or polynucleotide or diagnosing a nociceptive-associated disorder in a subject including contacting a cell component containing ANKTM1-related polypeptide or polynucleotide with a reagent which binds to the cell polypeptide or polynucleotide (herein after cell component). The cell component can be or contain a nucleic acid, such as DNA or RNA, or a protein. When the component is nucleic acid, the reagent is a nucleic acid probe or PCR primer. When the cell component is protein, the reagent is an antibody probe. The probes are detectably labeled, for example, with a radioisotope, a fluorescent compound, a bioluminescent compound, a chemiluminescent compound, a metal chelator or an enzyme. Those of ordinary skill in the art will know of other labels suitable for binding to an antibody or nucleic acid probe, or will be able to ascertain such, using routine experimentation. There are many different labels and methods for labeling known to those of ordinary skill in the art. Examples of the types of labels, which can be used in the present invention, include enzymes, radioisotopes, colloidal metals, fluorescent compounds, chemiluminescent compounds, and bioluminescent compounds. In addition, the antibodies, polypeptides and polynucleotide sequences of the invention can be used to diagnosis a nociceptive disorder.

A monoclonal antibody of the invention, directed toward ANKTM1-related polypeptide is useful for the in vivo and in vitro detection of antigen. The detectably labeled monoclonal antibody is given in a dose that is diagnostically effective. The term "diagnostically effective" means that the amount of detectably labeled monoclonal antibody is administered in sufficient quantity to enable detection of ANKTM1-related polypeptide antigen for which the monoclonal antibodies are specific.

The concentration of a detectably labeled monoclonal antibody administered to a subject should be sufficient such that the binding to those cells, body fluid, or tissue having ANKTM1-related polypeptide that is detectable compared to the background. Further, it is desirable that the detectably labeled monoclonal antibody be rapidly cleared from the circulatory system in order to give the best target-to-background signal ratio.

For in vivo diagnostic imaging, the type of detection instrument available is a major factor in selecting a given radioisotope. The radioisotope chosen must have a type of decay that is detectable for a given type of instrument. Still another important factor in selecting a radioisotope for in vivo diagnosis is the half-life of the radioisotope which should be long enough so that it is still detectable at the time of maximum uptake by the target, but short enough so that deleterious radiation with respect to the host is minimized. Ideally, a radioisotope used for in vivo imaging will lack a particle emission, but produce a large number of photons in the 140-250 nm key range, which may be readily detected by conventional gamma cameras.

For in vivo diagnosis, radioisotopes may be bound to immunoglobulin either directly or indirectly by using an intermediate functional group. Intermediate functional groups, which often are used to bind radioisotopes that exist as metallic ions to immunoglobulins, are the bifunctional chelating agents such as diethylenetriaminepentacetic acid (DTPA) and ethylenediaminetetraacetic acid (EDTA) and similar molecules. Typical examples of metallic ions that can be bound to the monoclonal antibodies of the invention are $^{111}$In, $^{97}$Ru, $^{67}$Ga, $^{68}$Ga, $^{72}$As, $^{89}$Zr, and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements that are particularly useful in such techniques include $^{157}$Gd, $^{55}$Mn, $^{162}$Dy, $^{52}$Cr, and $^{56}$Fe.

In another embodiment, nucleic acid probes can be used to identify a polynucleotide encoding an invention ANKTM1-related polypeptide from a specimen obtained from a subject. Examples of specimens from which nucleic acid sequence encoding an invention ANKTM1-related polypeptide can be derived include insect, human, swine, porcine, feline, canine, equine, murine, cervine, caprine, lupine, leporidine and bovine species.

Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., Nucl. Acid Res. 9:879, 1981).

In an embodiment of the invention, purified nucleic acid fragments containing intervening sequences or oligonucleotide sequences of 10-50 base pairs are radioactively labeled. The labeled preparations are used to probe nucleic acids from a specimen by the Southern hybridization technique. Nucleotide fragments from a specimen, before or after amplification, are separated into fragments of different molecular masses by gel electrophoresis and transferred to filters that bind nucleic acid. After exposure to the labeled probe, which will hybridize to nucleotide fragments containing target nucleic acid sequences, binding of the radioactive probe to target nucleic acid fragments is identified by autoradiography (see Genetic Engineering, 1, ed. Robert Williamson, Academic Press, (1981), 72-81). Alternatively, nucleic acid from the specimen can be bound directly to filters to which the radioactive probe selectively attaches by binding nucleic acids having the sequence of interest. Specific sequences and the degree of binding are quantitated by directly counting the radioactive emissions.

Where the target nucleic acid is not amplified, detection using an appropriate hybridization probe may be performed directly on the separated nucleic acid. In those instances where the target nucleic acid is amplified, detection with the appropriate hybridization probe would be performed after amplification.

For the most part, the probe will be detectably labeled with an atom or inorganic radical, most commonly using radionuclides, but also heavy metals can be used. Conveniently, a radioactive label may be employed. Radioactive labels include $^{32}$P, $^{125}$I, $^{3}$H, $^{14}$C, $^{111}$In, $^{99}$Tc, or the like. Any radioactive label may be employed which provides for an adequate signal and has sufficient half-life. Other labels include ligands, which can serve as a specific binding pair member for a labeled ligand, and the like. A wide variety of labels routinely employed in immunoassays can readily be employed in the present assay. The choice of the label will be governed by the effect of the label on the rate of hybridization and binding of the probe to mutant nucleotide sequence. It will be necessary that the label provide sufficient sensitivity to detect the amount of mutant nucleotide sequence available for hybridization.

The manner in which the label is bound to the probe will vary depending upon the nature of the label. For a radioactive label, a wide variety of techniques can be employed. Commonly employed is nick translation with a $^{32}$P-dNTP or terminal phosphate hydrolysis with alkaline phosphatase followed by labeling with radioactive $^{32}$P employing $^{32}$P-NTP and T4 polynucleotide kinase. Alternatively, nucleotides can be synthesized where one or more of the elements present are replaced with a radioactive isotope, e.g., hydrogen with tritium. If desired, complementary labeled strands can be used as probes to enhance the concentration of hybridized label.

Where other radionucleotide labels are involved, various linking groups can be employed. A terminal hydroxyl can be esterified with inorganic acids, e.g., $^{32}$P phosphate, or $^{14}$C organic acids, or else esterified to provide linking groups to the label. Alternatively, intermediate bases may be substituted with activatable linking groups that can then be linked to a label.

Enzymes of interest as reporter groups will primarily be hydrolases, particularly esterases and glycosidases, or oxidoreductases, particularly peroxidases. Fluorescent compounds include fluorescein and its derivatives, rhodamine and its derivatives, dansyl, umbelliferone, and so forth. Chemiluminescers include luciferin, and 2,3-dihydrophthalazinediones (e.g., luminol).

Standard hybridization techniques for detecting a nucleic acid sequence are known in the art. The particular hybridization technique is not essential to the invention. Other hybridization techniques are described by Gall and Pardue, Proc. Natl. Acad. Sci. 63:378, 1969); and John, et al., Nature, 223: 582, 1969). As improvements are made in hybridization techniques they can readily be applied in the method for the invention.

The amount of labeled probe present in the hybridization solution will vary widely, depending upon the nature of the label, the amount of the labeled probe that can reasonably bind to the filter, and the stringency of the hybridization. Generally, substantial excess over stoichiometric concentrations of the probe will be employed to enhance the rate of binding of the probe to the fixed target nucleic acid.

The present invention also contemplates transgenic non-human organisms, including invertebrates, vertebrates and mammals. For purposes of the subject invention, these animals are referred to as "transgenic" when such animal has had a heterologous DNA sequence, or one or more additional DNA sequences normally endogenous to the animal (collectively referred to herein as "transgenes") chromosomally integrated into the germ cells of the animal. The transgenic animal (including its progeny) will also have the transgene integrated into the chromosomes of somatic cells.

Various methods to make the transgenic animals of the subject invention can be employed. Generally speaking, three such methods may be employed. In one such method, an embryo at the pronuclear stage (a "one cell embryo") is harvested from a female and the transgene is microinjected into the embryo, in which case the transgene will be chromosomally integrated into both the germ cells and somatic cells of the resulting mature animal. In another such method, embryonic stem cells are isolated and the transgene incorporated therein by electroporation, plasmid transfection or microinjection, followed by reintroduction of the stem cells into the embryo where they colonize and contribute to the germ line. Methods for microinjection of mammalian species are described in U.S. Pat. No. 4,873,191. In yet another such method, embryonic cells are infected with a retrovirus containing the transgene whereby the germ cells of the embryo have the transgene chromosomally integrated therein. When the animals to be made transgenic are avian, because avian fertilized ova generally go through cell division for the first twenty hours in the oviduct, microinjection into the pronucleus of the fertilized egg is problematic due to the inaccessibility of the pronucleus. Therefore, of the methods to make transgenic animals described generally above, retrovirus infection is preferred for avian species, for example as described in U.S. Pat. No. 5,162,215. If microinjection is to be used with avian species, however, a published procedure by Love et al., (Biotechnology, 12, Jan. 1994) can be utilized whereby the embryo is obtained from a sacrificed hen approximately two and one-half hours after the laying of the previous laid egg, the transgene is microinjected into the cytoplasm of the germinal disc and the embryo is cultured in a host shell until maturity. When the animals to be made transgenic are bovine or porcine, microinjection can be hampered by the opacity of the ova thereby making the nuclei difficult to identify by traditional differential interference-contrast microscopy. To overcome this problem, the ova can first be centrifuged to segregate the pronuclei for better visualization.

The "non-human animals" of the invention include, for example, bovine, porcine, ovine and avian animals (e.g., cow, pig, sheep, chicken, turkey). The "transgenic non-human animals" of the invention are produced by introducing "transgenes" into the germ line of the non-human animal. Embryonal target cells at various developmental stages can be used to introduce transgenes. Different methods are used depending on the stage of development of the embryonal target cell. The zygote is the best target for micro-injection. The use of zygotes as a target for gene transfer has a major advantage in that in most cases the injected DNA will be incorporated into the host gene before the first cleavage (Brinster et al., Proc. Natl. Acad. Sci. USA 82:4438-4442, 1985). As a consequence, all cells of the transgenic non-human animal will carry the incorporated transgene. This will in general also be reflected in the efficient transmission of the transgene to offspring of the founder since 50% of the germ cells will harbor the transgene.

The term "transgenic" is used to describe an animal that includes exogenous genetic material within all of its cells. A "transgenic" animal can be produced by crossbreeding two chimeric animals that include exogenous genetic material within cells used in reproduction. Twenty-five percent of the resulting offspring will be transgenic i.e., animals which include the exogenous genetic material within all of their cells in both alleles. 50% of the resulting animals will include the exogenous genetic material within one allele and 25% will include no exogenous genetic material.

In the microinjection method useful in the practice of the invention, the transgene is digested and purified free from any vector DNA e.g. by gel electrophoresis. It is preferred that the transgene include an operatively associated promoter which interacts with cellular proteins involved in transcription, ultimately resulting in constitutive expression. Promoters useful in this regard include those from cytomegalovirus (CMV), Moloney leukemia virus (MLV), and herpes virus, as well as those from the genes encoding metallothionein, skeletal actin, P-enolpyruvate carboxylase (PEPCK), phosphoglycerate (PGK), DHFR, and thymidine kinase. Promoters for viral long terminal repeats (LTRs) such as Rous Sarcoma Virus can also be employed. When the animals to be made transgenic are avian, preferred promoters include those for the chicken-globin gene, chicken lysozyme gene, and avian leukosis virus. Constructs useful in plasmid transfection of embryonic stem cells will employ additional regulatory elements well known in the art such as enhancer elements to stimulate transcription, splice acceptors, termination and polyadenylation signals, and ribosome binding sites to permit translation.

Retroviral infection can also be used to introduce transgene into a non-human animal, as described above. The developing non-human embryo can be cultured in vitro to the blastocyst stage. During this time, the blastomeres can be targets for retro viral infection (Jaenich, R., Proc. Natl. Acad. Sci USA 73:1260-1264, 1976). Efficient infection of the blastomeres is obtained by enzymatic treatment to remove the zona pellucida (Hogan, et al. (1986) in Manipulating the Mouse Embryo, Cold Spring Harbor Laboratory Press, Cold Spring Harbor, N.Y.). The viral vector system used to introduce the transgene is typically a replication-defective retro virus carrying the transgene (Jahner, et al., Proc. Natl. Acad. Sci. USA 82:6927-6931, 1985; Van der Putten, et al., Proc. Natl. Acad. Sci USA 82:6148-6152, 1985). Transfection is easily and efficiently obtained by culturing the blastomeres on a monolayer of virus-producing cells (Van der Putten, supra; Stewart, et al., EMBO J. 6:383-388, 1987). Alternatively, infection can be performed at a later stage. Virus or virus-producing cells can be injected into the blastocoel (D. Jahner et al., Nature 298:623-628, 1982). Most of the founders will be mosaic for the transgene since incorporation occurs only in a subset of the cells that formed the transgenic nonhuman animal. Further, the founder may contain various retro viral insertions of the transgene at different positions in the genome that generally will segregate in the offspring. In addition, it is also possible to introduce transgenes into the germ line, albeit with low efficiency, by intrauterine retroviral infection of the midgestation embryo (D. Jahner et al., supra).

A third type of target cell for transgene introduction is the embryonal stem cell (ES). ES cells are obtained from pre-implantation embryos cultured in vitro and fused with embryos (M. J. Evans et al. Nature 292:154-156, 1981; M. O. Bradley et al., Nature 309:255-258, 1984; Gossler, et al., Proc. Natl. Acad. Sci USA 83:9065-9069, 1986; and Robertson et al., Nature 322:445-448, 1986). Transgenes can be efficiently introduced into the ES cells by DNA transfection or by retro virus-mediated transduction. Such transformed ES cells can thereafter be combined with blastocysts from a nonhuman animal. The ES cells thereafter colonize the embryo and contribute to the germ line of the resulting chimeric animal. (For review see Jaenisch, R., Science 240: 1468-1474, 1988).

"Transformed" means a cell into which (or into an ancestor of which) has been introduced, by means of recombinant nucleic acid techniques, a heterologous nucleic acid molecule. "Heterologous" refers to a nucleic acid sequence that either originates from another species or is modified from either its original form or the form primarily expressed in the cell.

"Transgene" means any piece of DNA that is inserted by artifice into a cell, and becomes part of the genome of the organism (i.e., either stably integrated or as a stable extrachromosomal element) that develops from that cell. Such a transgene may include a gene that is partly or entirely heterologous (i.e., foreign) to the transgenic organism, or may represent a gene homologous to an endogenous gene of the organism. Included within this definition is a transgene created by the providing of an RNA sequence that is transcribed into DNA and then incorporated into the genome. The transgenes of the invention include DNA sequences which encode an invention ANKTM1-related polypeptide, and include sense, antisense, dominant negative encoding polynucleotides, which may be expressed in a transgenic non-human animal. The term "transgenic" as used herein additionally includes any organism whose genome has been altered by in vitro manipulation of the early embryo or fertilized egg or by any transgenic technology to induce a specific gene knockout (i.e., knockout of an invention ANKTM1-related polypeptide). The term "gene knockout" as used herein, refers to the targeted disruption of a gene in vivo with complete or partial loss of function that has been achieved by any transgenic technology familiar to those in the art (e.g., insertion of a P-element in Drosophila). In one embodiment, transgenic animals having gene knockouts are those in which the target gene has been rendered nonfunctional by an insertion targeted to the gene to be rendered non-functional by homologous recombination. As used herein, the term "transgenic" includes any transgenic technology familiar to those in the art which can produce an organism carrying an introduced transgene or one in which an endogenous gene has been rendered non-functional or "knocked out."

In one embodiment, the transgene comprises DNA antisense to the coding sequence for an invention ANKTM1-related polypeptide. In another embodiment, the transgene comprises DNA encoding an antibody that is able to bind to an invention ANKTM1-related polypeptide. Where appropriate, DNA sequences that encode proteins having nociceptive activity but differ in nucleic acid sequence due to the degeneracy of the genetic code may also be used herein, as may truncated forms, allelic variants and interspecies homologues.

The invention also includes animals having heterozygous mutations in or partial inhibition of function or expression of an invention ANKTM1-related polypeptide. One of skill in the art would readily be able to determine if a particular mutation or if an antisense molecule was able to partially inhibit ANKTM1-related polypeptide. For example, in vitro testing may be desirable initially by comparison with wild-type (e.g., comparison of northern blots to examine a decrease in expression).

After an embryo has been microinjected, colonized with transfected embryonic stem cells or infected with a retrovirus containing the transgene (except for practice of the subject invention in avian species which is addressed elsewhere herein) the embryo is implanted into the oviduct of a pseudopregnant female. The consequent progeny are tested for incorporation of the transgene by Southern blot analysis of blood samples using transgene specific probes. PCR is particularly useful in this regard. Positive progeny ($G_0$) are crossbred to produce offspring ($G_1$), which are analyzed for transgene expression by Northern blot analysis of tissue samples. To be able to distinguish expression of like-species transgenes from expression of the animal's endogenous ANKTM1-related polypeptide gene(s), a marker gene fragment can be included in the construct in the 3' untranslated region of the transgene and the Northern probe designed to probe for the marker gene fragment. The serum levels of ANKTM1-related polypeptide can also be measured in the transgenic animal to establish appropriate expression.

Expression of the nociceptive-related transgenes, thereby decreasing the ANKTM1-related polypeptide in the tissue and serum levels of the transgenic animals.

Transgenic organisms of the invention are highly useful in the production of organisms for study of tumorgenesis and in identifying agents or drugs with inhibit or modulate tumorgenesis and inheritance.

It will be recognized that the method for creating a transgenic organism include methods for inserting a transgene into, for example, an embryo of an already created transgenic organism, the organism being transgenic for a different unrelated gene or gene product.

In one embodiment the transgenic organism is an insect. An insect as used herein denotes all insect species. Typically the insect is selected from the group consisting of bristletails, springtails, mayflies, dragonflies, damselflies, grasshoppers, crickets, walkingsticks, praying-mantises, cockroaches, earwigs, termites, stoneflies, lice, thrips, bed bugs, plant bugs, damsel bugs, flower bugs, assassin bugs, ambush bugs, lace bugs, stink bugs, cicadas, treehoppers, leafhoppers, spittlebugs, planthoppers, aphids, whiteflies, beetles, scropionflies, caddisflies, moths, skippers, butterflies, crane flies, sand flies, mosquitoes, horse flies, fruit flies louse flies, bees, wasps, and ants.

The transgenic insects of the invention can be produced by introducing into single cell embryos DNA disrupting expression of a nucleic acid encoding the wild type ANKTM1-related polypeptide sequence. Transgenic insects can be generated by microinjection, which can produce P-element mediated germ line transformation. For transgenic insects, generally the transgene is introduced at an embryonic stage. For example, transgenic insects of the present invention can be produced by introducing into single cell embryos invention polynucleotides, either naked or contained in an appropriate vector, by microinjection, for example, which can produce insects by P-element mediated germ line transformation (see e.g., Rubin et al., *Science* 218:348-353 (1982)). Totipotent or pluripotent stem cells transformed by microinjection, calcium phosphate mediated precipitation, liposome fusion, retroviral infection or other means are then introduced into the embryo, and the polynucleotides are stably integrated into the genome. A transgenic embryo so transformed then develops into a mature transgenic insect in which the transgene is inherited in normal Mendelian fashion. Additional methods for producing transgenic insects can be found, for example, in O=Brochta et al., *Insect Biochem. Mol. Biol.* 26:739-753 (1996) and in Louleris et al., *Science* 270:2002-2005 (1995).

In one method, developing insect embryos are infected with a virus, such as a baculovirus (e.g., *Autographa californica* AcNPV), containing a polynucleotide sequence of the invention, and transgenic insects produced from the infected embryo. The virus can be an occluded virus or a nonoccluded virus. A virus can be occluded by coinfection of cells with a helper virus that supplies polyhedrin gene function. The skilled artisan will understand how to construct recombinant viruses in which the polynucleotide is inserted into a nonessential region of the baculovirus genome. For example, in the AcNPV genome, nonessential regions include the p10 region (Adan et al., *Virology* 444:782-793, 1982), the DA26 region (O'Reily et al., *J. Gen. Virol.* 71:1029-1037, 1990), the ETL region (Crawford et al., *Virology* 62:2773-2781, 1988), the egt region (O'Reily et al., *J. Gen. Virol.* 64:1321-1328), amongst others. Significant homology exists among particular genes of different baculoviruses and therefore, one of skill in the art will understand how to insert an invention polynucleotide into similar nonessential regions of other baculoviruses. Thus, for example, a sequence encoding an invention ANKTM1-related polypeptide as described herein may be placed under control of an AcNPV promoter (e.g., the polyhedrin promoter). Depending on the vector utilized, any of a number of suitable transcription and translation elements, including constitutive, inducible and conditional promoters, enhancers, transcription terminators, etc. may be used in order to transcribe invention polynucleotides or express invention polypeptides. Alternatively, a transgene containing a nucleic acid sequence disrupting expression of an invention ANKTM1-related polypeptide may not contain a promoter as the nucleic acid sequence need not be transcribed or translated to obtain a transgenic insect having disrupted ANKTM1-related polypeptide.

Thus, the invention provides methods for producing transgenic insects having a disrupted nucleic acid sequence encoding an invention ANKTM1-related polypeptide. The methods include introducing into the genome of an insect a nucleic acid construct, including a disrupted or mutated ANKTM1-related polynucleotide sequence, and obtaining a transgenic insect having a disrupted nucleic acid sequence encoding ANKTM1-related polypeptide. The invention further provides methods for producing transgenic insects having a nucleic acid encoding ANKTM1-related polypeptide or functional fragment thereof.

The results disclosed herein were also described in Cell, Vol. 112, 819-829, Mar. 21, 2003, which publication is incorporated herein by reference, in particular the Figures, Examples and Results reported therein.

Without further elaboration, it is believed that one skilled in the art can, using the preceding description, utilize the present invention to its fullest extent. The following examples are to be considered illustrative and thus are not limiting of the remainder of the disclosure in any way whatsoever.

EXAMPLE 1

Molecular Cloning of ANKTM1

Bioinformatic searches were done as previously described (Peier et al., 2002a, supra; Peier et al., 2002b, supra). Sequence analysis was performed using the Biology Workbench at the San Diego Supercomputing Center. A 902-base pair fragment of the mouse homologue of ANKTM1 was amplified from newborn mouse DRG cDNA using the following primers:

```
                                                  (SEQ ID NO:9)
    mANK-like F2  (5'-AGTGGGGAGACTACCCTGTG)
    and
                                                 (SEQ ID NO:10)
    mANK-like R2  (5'-TTTATCATGCCCATTCTTTGC).
```

From this initial sequence and subsequent hits to DNA databases, the following primers were designed to PCR-amplify full-length ANKTM1 from adult mouse trigeminal ganglia cDNA:

```
    mANK-like start
                                                 (SEQ ID NO:11)
    (5'TTTGGATCCGCCACCATGAAGCGCGGCTTGAGGAGG)
    and mANK-like stop
                                                  (SEQ ID NO 12)
    (5'TTTGCGGCCGCCTAAAAGTCCGGGTGGCTAATAGAAC).
```

EXAMPLE 3

Expression Analysis

Overall tissue distribution of ANKTM1 was analyzed by Northern blot analysis using a probe corresponding to nucleotides 590-1492 of mouse ANKTM1 (SEQ ID NO:13). To further determine the expression pattern of ANKTM1, a rat tissue Northern blot was prepared as follows: total RNA was purified from adult tissues using Trizol (Invitrogen/Gibco Life Technologies, San Diego, Calif.), followed by polyA+ purification with OLIGOTEX™ (Qiagen, Valencia, Calif.) according to manufacturer protocols. Approximately 3 µg polyA$^+$ RNA was electrophoresed on a 1% glyoxal gel, transferred to nylon membranes and hybridized with a $^{32}$P-labeled probe corresponding to nucleotides 590-1492 of mouse full-length ANKTM1 (SEQ ID NO:13). Blots were hybridized 3 hours at 65° C. in EXPRESSHYB™ solution (Clonetech, Palo Alto, Calif.) and analyzed using a phosphorimager. A commercial mouse tissue northern blot (Clonetech) was similarly treated.

Figure 2A:
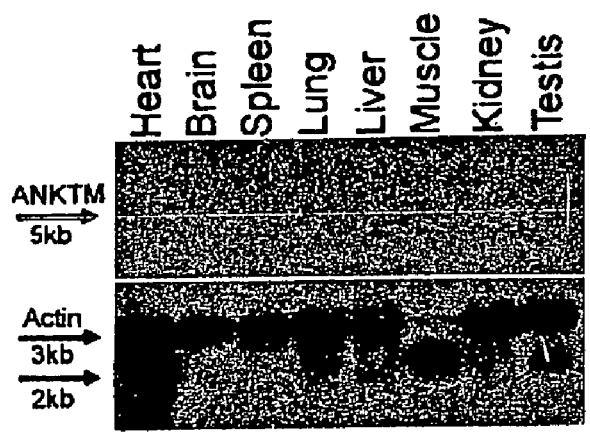
FIG. 2A is a Northern blot analysis of mouse tissue showing ANKTM is not expressed in tissues tested.
Figure 2B:
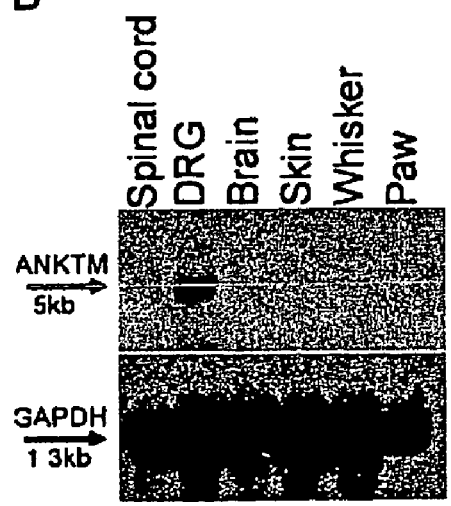
FIG. 2B is a Northern blot analysis of rat tissues showing expression of ANKTM1 in the dorsal root ganglia (DRG). Blots were hybridized with a $^{32}$P-labeled fragment of ANKTM1 cDNA (top panel) and with control cDNAs (bottom panel).

The tissue distribution studies showed that ANKTM1 expression was not detected on a blot containing various mouse tissues, including heart, lung, skeletal muscle, and kidney (FIG. 2A). However, probe of a blot containing rat tissues relevant to sensory neurons and their projections such as DRG, spinal cord, and skin detected a single mRNA species of approximately 5 kb only in DRG (FIG. 2B).

In Situ Hybridization Studies

More detailed expression analysis of ANKTM1 in DRG was carried out via in situ hybridization and immunostaining. For in situ hybridization and immunostaining of DRG's, adult mice were perfused with 4% paraformaldehyde and DRG's rapidly dissected. Following post-fixation and cryo-protection in 30% sucrose in PBS, single DRG's were embedded in OCT compound, frozen in liquid nitrogen and sectioned at 10-µm thickness. Digoxigenin-labeled ANKTM1 cRNA probes strongly hybridized to neurons in adult DRG and trigeminal ganglia (FIG. 3). ANKTM1 expression was found to be restricted to a small sub-population of DRG neurons (59 of 1608 or 3.6% of the DRG neurons). To further characterize its expression in sensory neurons, tests were conducted to determine whether other DRG markers co-localized with ANKTM1. These tests showed that ANKTM1 is not expressed in heavily myelinated neurons marked by NF-150 kd (FIGS. 3A-3C). This finding shows that ANKTM1 is most likely expressed in the non-myelinated C- or lightly myelinated A$_\delta$-fiber population of neurons that sense temperature and/or noxious stimuli.

EXAMPLE 3

Double In-Situ Hybridization Studies

The expression of ANKTM1 relative to known thermo-activated TRP channels was also studied. TRPV1 (VR1) is a well-characterized receptor for noxious heat, pH, and capsaicin. For double in-situ hybridizations, sections were hybridized with in vitro transcribed digoxigenin- or fluorescein-labeled cRNA probes (Roche, Basel, Switzerland) corresponding to nucleotides 590-1492 of mANKTM1, and nucleotides 1410-1980 of mTRPM8 (NM_029310) (SEQ ID NO:14). We used two cRNA probes corresponding to bases 1516-2065 or 1516-2482 of TRPV1 sequence (AF029310). Both probes showed consistent patterns of hybridization. Peroxidase-conjugated anti-digoxigenin-POD (1:500) and alkaline phosphatase-conjugated anti-fluorescein (1:2000) antibodies (Roche) were used to detect hybridized cRNA probes and visualized using tyramide signal amplification (TSA; NEN) and fast-red detection (Roche) systems, respectively. The immunostaining experiments followed hybridization of sections with digoxigenin-labeled cRNA probes and TSA fluorescent detection. Anti-NF 150 kd (1-1000; Chemicon, Temecula, Calif.) and anti-CGRP (1:100; Biogenesis,) primary antibodies and anti-rabbit Cy3 (1:200, Jackson Immunoresearch,) secondary antibodies were used.

The results of these experiments utilizing ANKTM1 and TRPV1 probes (FIGS. 3G-3I) revealed that 97%, or 100 out of 103, of ANKTM1-positive neurons also express TRPV1, while 30% (or 100 out of 336) of TRPV1-positive neurons express ANKTM1. This expression pattern differs from that of TRPM8, the cold and menthol receptor, which is not not coexpressed with CGRP and TRPV1 in DRG neurons. Since ANKTM1 expression overlaps with these two markers, coexpression of ANKTM1 and TRPM8 would not be expected. However, these double in situ hybridizations revealed no overlap of expression between ANKTM1 and TRPM8 (n=113 for ANKTM1 and 137 for TRPMS) (FIGS. 3J-3L). Taken together, these results indicate that ANKTM1 is expressed in a sub-population of nociceptive/thermoceptive neurons that coincides with noxious heat-activated TRPV1 receptor, but not with the cool/cold-activated TRPM8 receptor.

In accordance with this observation, it was further discovered that ANKTM1 is expressed in Calcitonin gene-related peptide (CGRP)- and in Substance P (SP)-positive neurons (FIGS. 3D-3F). 97% or 69 out of 71 of these ANKTM1-positive neurons were CGRP-positive. Both CGRP and SP are secreted inflammatory peptides expressed in a subset of nociceptive neurons (Scott, 1992).

EXAMPLE 4

CHO Cell Expression System

Nevertheless, since ANKTM1 bears similarities to TRP-like channels expressed in sensory neurons, tests were conducted to determine activation of ANKTM1 by various sensory stimuli. To this end, a series of tests were conducted using full-length murine ANKTM1 stably transfected in Chinese Hamster Ovary (CHO) cells containing FRT sites (CHO-K1/FRT) under control of a tetracycline (Tet)-inducible promoter via Flp recombinase mediated recombination.

CHO-K1/FRT cells were stably transfected with full-length murine ANKTM1 in the pcDNA5/FRT vector using Lipofectamine (Invitrogen) according to the manufacturer's protocol. Transfected cells were selected in growth medium containing Hygromycin (200 µg/mL). Northern blot analysis identified stable clones expressing ANKTM1 mRNA. The generation of stable murine TRPM8-expressing CHO-K1/FRT cells has been previously described (Peier et al, 2002). ANKTM1-expressing stable CHO-K1/FRT lines appeared unhealthy (membrane blebbing, cytoplasmic granulations) in culture, and after several passages, a loss of ANTKM1 expression was observed. Previous investigators have also claimed difficulty generating stable cell lines expressing human ANKTM1.

To circumvent this problem, cell lines were generated in which ANKTM1 expression could be controlled. Tetracycline-inducible CHO-K1/FRT cells lines were generated by transfecting the CHO Flp-In host cell line with pcDNA6/TR according to manufacturer's instructions (Invitrogen, San Diego, Calif.) and selected in 5 µg/mL Blasticidin. Clones stably expressing the tetracycline repressor identified by blasticidin resistance were transiently transfected with a control plasmid containing the CAT gene and selected based on high levels of CAT expression after treatment with tetracycline. The gene expression vector; pcDNA5FRT/TO containing full-length murine ANKTM1 and the Flp recombinase expression plasmid pOG44 were co-transfected into the tetracycline-inducible CHO-K1/FRT cell line and selected via Hygromycin resistance (200 μg/ml). Induction of ANKTM1 was accomplished by treating CHO cells with 1-2 μg/mL tetracycline (Tet) 5-24 hours before experiments.

Stable clones expressing ANKTM1 were identified by Northern blot analysis. Northern blot analysis of control and Tet-treated ANTKM1-inducible CHO cells showed high levels of ANKTM1 expression. A low but not absent level in the absence of Tet was also present in these cells. Therefore, CHO cells that stably expressed the Tet-repressor were used as controls in subsequent experiments. For some of the experiments, cells were maintained in culture medium supplemented with 5 μm ruthenium red (RR, Fluka), which blocks ANKTM1 activity. This was done to overcome the slight leaky expression of ANKTM1 in the Tet-system. Cells cultured in RR looked healthier and a higher percentage of cells responded to cold compared to non-RR treated cells.

As shown in FIG. 4A, when buffer is cooled, $[Ca^{2+}]_i$ increases rapidly in ANKTM1-expressing CHO cells, but not in untransfected CHO cells. Average activation temperature (measured at the inlet of the cell chamber by a miniature thermocouple) is approximately 17° C. Cooling in the presence of 5 μm ruthenium red and in the absence of extracellular $Ca^{2+}$ eliminates cold-evoked responses. The threshold of activation was not affected.

EXAMPLE 5

Intracellular Calcium Imaging Experiments

Calcium imaging experiments were performed essentially as described (Peier et al., 2002a, supra). Briefly, cells were plated on glass coverslips 24-48 hours prior to imaging experiments. Cells were washed in HEPES buffeted saline solution (2 mM $Ca^{2+}$), loaded with Fura-2 acetoxymethyl ester (5 mM), 1.5 mM pluronic acid (Molecular Probes, Eugene, Oreg.) and incubated for 1 hour at room temperature in the dark. Coverslips were placed in laminar flow chamber (Warner Instrument Corp., Hamden, Conn.) and perfused with HEPES buffered saline (2 mM $Ca^{2+}$) flowing through small-diameter tubing at the inlet of the chamber. Perfusion rate was approximately 2 ml/min and was stopped and started via a solenoid switch (Warner Instrument Corp., Hamden, Conn. Perfusate temperature was controlled by a Peltier device and monitored via miniature thermocouple at the inlet of the chamber. Heated (up to 52° C.), chilled (down to 9° C., the limit of our system), and room temperature buffer was delivered through the same application tubing at the inlet of the chamber. Alternatively, in experiments where the compounds menthol (Sigma, St. Louis, Mo.]), capsaicin (Fluka, Buchs, Switzerland) and Icilin (Tocris Woodson,) were applied, cells were plated on 24-well tissue culture plates and loaded with Fura-2. Compounds were delivered with a 3 cc syringe during a period of ten seconds.

Images of Fura-2 loaded cells with the excitation wavelength alternating between 340 nm and 380 nm were captured with a cooled LCD camera. The ratio of fluorescence intensity of the two wavelengths of groups of 30-50 cells in each experiment was analyzed using MetaFluor (Universal Imaging Corp). Experiments were performed in triplicate. Unless otherwise indicated, graphs represent averaged responses of 20-40 cells from representative experiments. For direct comparison of results from different experiments, values were normalized to baseline of the ratio 340/380. For ANKTM1 and TRPM8 threshold experiments, the threshold temperature of activation of 60-100 cells each from three replicate experiments was analyzed. Threshold of activation was defined as 20% above baseline. Hanks Balanced Salt Solution (HBSS) and HEPES buffers were obtained from GibcoBRL. The results of these experiments are shown in FIG. 5 herein.

EXAMPLE 6

Electrophysiology

Cells were plated onto poly-D-lysine-coated coverslips for recording purposes, and recordings were undertaken 18-24 hr later. Experiments were carried out at room temperature using whole-cell voltage clamp technique, with an Axopatch 2B amplifier filtered at 5 kHz and pClamp suite of software (Axon Instruments). Series-resistance compensation was 80% for all experiments, using 2-5 MΩ fire-polished pipettes. Recording solutions were as follows: pipette solution for all experiments was [(mM) CsCl, 140; BAPTA, 10; HEPES, 10; MgATP, 2; titrated to pH7.4 with CsOH. The external solution in the recording chamber was kept at 32° C. and consisted of [(mM): CholineCl, 100; NaCl, 40; HEPES, 10; $CaCl_2$, 2; $MgCl_2$ 1; titrated to pH 7.4 with NaOH]. In some studies the above solution was used with 140 mM NaCl and no Choline. In monovalent permeability studies, equimolar KCl or CsCl replaced NaCl (40 mM). In divalent permeability studies, the solutions either contained 1 mM of test ion and (mM) CholineCl, 100; NaCl, 40; Hepes, 10; sucrose, 80 or 30 mM test ion in the above solution without sucrose. The current-voltage relationships were determined using a 2 second ramp from −100 to +80 mV.

Permeability ratios relative to $Na^+$, were calculated for monovalent cations as follows: $P_X/P_{Na}=E_{shift}=\{RT/F\} \log (P_X/P_{Na} [X]_O/[Na]_O)$, where F is Faraday's constant, R is the universal gas constant, and T is absolute temperature. Permeability ratios relative to $Na^+$, for divalent cations were calculated as follows: $Eshift=\{RT/F\} \log \{[Na]_O+4B' [Ca]_{O(2)}\}/\{[Na]_O 4B' [Ca]_{O(1)}\}$, where $B'=P'_{Ca}/P_{Na}$ and $P'_{Ca}=P_{Ca}/(1+e^{EF/RT})$ and $[Ca]_{O(1)}$ and $[Ca]_{O(2)}$ refer to the two different concentrations of the divalent ion tested.

ANKTM1 and TRPM8 were cloned into the pOX expression vector for expression in *Xenopus* oocytes (Jegla and Salkoff, 1997). Capped cRNAs were prepared by run-off transcription using the T3 in Message mMachine kit (Ambion) and cleaned prior to injection using QIAQUICK™ columns (Qiagen). Mature oocytes were isolated enzymatically using known methodology. Oocytes were injected with 5 ng to 25 ng of cRNA in a 50 nl volume and incubated 2-5 days prior to recording at 18° C. in ND96 (96 mM NaCl, 2 mM KCl, 1.8 mM CaCl, 1 mM MgCl, 5 mM Hepes, 2.5 mM Na-pyruvate, 100 U/ml penicillin, 100 μg/ml streptomycin, pH7.5). Recordings were made using standard two-electrode voltage clamp techniques with 3 M KCl electrodes (0.3-0.5 MΩ). The recording solution consisted of 96 mM NaCl, 4 mM KCl, 1 mM MgCl, 100 μM CaCl and 5 mM Hepes, pH 7.5. Temperature control was achieved with a combination of a peltier-cooled stage and constant perfusion of cooled/heated solution. Temperatures were monitored using a miniature thermocouple placed adjacent to the oocyte in the recording chamber. Currents and temperatures were recorded using a TEV-200 amplifier (Dagan Instruments, Minneapolis, Minn.), an HCC-100A temperature controller (Dagan Instruments), and pCLAMP8™ software suite (Axon Instruments, Union City, Calif.). The oocytes were held at −70 mV during the recordings.

FIGS. 7A-D are a series of graphs summarizing the results of these experiments. FIGS. 7A and 7C show, respectively, inward currents recorded in response to first and second cold steps from *Xenopus* oocytes expressing ANKTM1; while FIGS. 7B and 7D show, respectively, inward currents recorded in response to cold steps from *Xenopus* oocytes expressing TRPM8. By comparison to TRPM8, ANKTM1 current responses were markedly reduced in the second cold step.

It will be apparent to those skilled in the art that various modifications and variations can be made to the compounds and processes of this invention. Thus, it is intended that the present invention cover such modifications and variations, provided they come within the scope of the appended claims. Accordingly, the invention is limited only by the following claims.

The invention claimed is:

1. An isolated nucleic acid encoding an ANKTM1-related polypeptide consisting of the amino acid sequence as set forth in SEQ ID NO: 2.

2. An expression vector comprising the nucleic acid of claim 1.

3. The vector of claim 2, wherein the vector is a plasmid.

4. The vector of claim 2, wherein the vector is a virus.

5. An isolated host cell stably transformed with the vector of claim 2.

6. The host cell of claim 5, wherein the cell is prokaryotic.

7. The host cell of claim 5, wherein the cell is eukaryotic.

* * * * *

SEQUENCE LISTING

<160> NUMBER OF SEQ ID NOS: 13

<210> SEQ ID NO 1
<211> LENGTH: 320
<212> TYPE: PRT
<213> ORGANISM: Mus musculus

<400> SEQUENCE: 1

```
Leu Asn Val Met Val Gln His Asn Arg Ile Glu Leu Leu Asn His Pro
1               5                   10                  15

Val Cys Arg Glu Tyr Leu Leu Met Lys Trp Cys Ala Tyr Gly Phe Arg
            20                  25                  30

Ala His Met Met Asn Leu Gly Ser Tyr Cys Leu Gly Leu Ile Pro Met
        35                  40                  45

Thr Leu Leu Val Val Lys Ile Gln Pro Gly Met Ala Phe Asn Ser Thr
    50                  55                  60

Gly Ile Ile Asn Gly Thr Ser Ser Thr His Glu Glu Arg Ile Asp Thr
65                  70                  75                  80

Leu Asn Ser Phe Pro Ile Lys Ile Cys Met Ile Leu Val Phe Leu Ser
                85                  90                  95

Ser Ile Phe Gly Tyr Cys Lys Glu Val Ile Gln Ile Phe Gln Gln Lys
            100                 105                 110

Arg Asn Tyr Phe Leu Asp Tyr Asn Asn Ala Leu Glu Trp Val Ile Tyr
        115                 120                 125

Thr Thr Ser Ile Ile Phe Val Leu Pro Leu Phe Leu Asn Ile Pro Ala
    130                 135                 140

Tyr Met Gln Trp Gln Cys Gly Ala Ile Ala Ile Phe Phe Tyr Trp Met
145                 150                 155                 160

Asn Phe Leu Leu Tyr Leu Gln Arg Phe Glu Asn Cys Gly Ile Phe Ile
                165                 170                 175

Val Met Leu Glu Val Ile Phe Lys Thr Leu Leu Arg Ser Thr Gly Val
            180                 185                 190

Phe Ile Phe Leu Leu Leu Ala Phe Gly Leu Ser Phe Tyr Val Leu Leu
        195                 200                 205

Asn Phe Gln Asp Ala Phe Ser Thr Pro Leu Leu Ser Leu Ile Gln Thr
    210                 215                 220

Phe Ser Met Met Leu Gly Asp Ile Asn Tyr Arg Asp Ala Phe Leu Glu
225                 230                 235                 240

Pro Leu Phe Arg Asn Glu Leu Ala Tyr Pro Val Leu Thr Phe Gly Gln
                245                 250                 255

Leu Ile Ala Phe Thr Met Phe Val Pro Ile Val Leu Met Asn Leu Leu
            260                 265                 270

Ile Gly Leu Ala Val Gly Asp Ile Ala Glu Val Gln Lys His Ala Ser
        275                 280                 285
```

```
Leu Lys Arg Ile Ala Met Gln Val Glu Leu His Thr Asn Leu Glu Lys
        290                 295                 300
Lys Leu Pro Leu Trp Tyr Leu Arg Lys Val Asp Gln Arg Ser Thr Ile
305                 310                 315                 320

<210> SEQ ID NO 2
<211> LENGTH: 319
<212> TYPE: PRT
<213> ORGANISM: Homo sapiens

<400> SEQUENCE: 2

Leu Asn Ala Met Val Gln Asn Asn Arg Ile Glu Leu Leu Asn His Pro
1               5                   10                  15
Val Cys Lys Glu Tyr Leu Leu Met Lys Trp Leu Ala Tyr Gly Phe Arg
                20                  25                  30
Ala His Met Met Asn Leu Gly Ser Tyr Cys Leu Gly Leu Ile Pro Met
            35                  40                  45
Thr Ile Leu Val Val Asn Ile Lys Pro Gly Met Ala Phe Asn Ser Thr
    50                  55                  60
Gly Ile Ile Asn Glu Thr Ser Asp His Ser Glu Ile Leu Asp Thr Thr
65                  70                  75                  80
Asn Ser Tyr Leu Ile Lys Thr Cys Met Ile Leu Val Phe Leu Ser Ser
                85                  90                  95
Ile Phe Gly Tyr Cys Lys Glu Ala Gly Gln Ile Phe Gln Gln Lys Arg
            100                 105                 110
Asn Tyr Phe Met Asp Ile Ser Asn Val Leu Glu Trp Ile Ile Tyr Thr
        115                 120                 125
Thr Gly Ile Ile Phe Val Leu Pro Leu Phe Val Glu Ile Pro Ala His
    130                 135                 140
Leu Gln Trp Gln Cys Gly Ala Ile Ala Val Tyr Phe Tyr Trp Met Asn
145                 150                 155                 160
Phe Leu Leu Tyr Leu Gln Arg Phe Glu Asn Cys Gly Ile Phe Ile Val
                165                 170                 175
Met Leu Glu Val Ile Leu Lys Thr Leu Leu Arg Ser Thr Val Val Phe
            180                 185                 190
Ile Phe Leu Leu Leu Ala Phe Gly Leu Ser Phe Tyr Ile Leu Leu Asn
        195                 200                 205
Leu Gln Asp Pro Phe Ser Ser Pro Leu Leu Ser Ile Ile Gln Thr Phe
    210                 215                 220
Ser Met Met Leu Gly Asp Ile Asn Tyr Arg Glu Ser Phe Leu Glu Pro
225                 230                 235                 240
Tyr Leu Arg Asn Glu Leu Ala His Pro Val Leu Ser Phe Ala Gln Leu
                245                 250                 255
Val Ser Phe Thr Ile Phe Val Pro Ile Val Leu Met Asn Leu Leu Ile
            260                 265                 270
Gly Leu Ala Val Gly Asp Ile Ala Glu Val Gln Lys His Ala Ser Leu
        275                 280                 285
Lys Arg Ile Ala Met Gln Val Glu Leu His Thr Ser Leu Glu Lys Lys
    290                 295                 300
Leu Pro Leu Trp Phe Leu Arg Lys Val Asp Gln Lys Ser Thr Ile
305                 310                 315

<210> SEQ ID NO 3
<211> LENGTH: 352
<212> TYPE: PRT
```

<213> ORGANISM: Drosophila melanogaster

<400> SEQUENCE: 3

```
Leu Asn Thr Met Val Thr His Gly Arg Val Glu Leu Leu Ala His Pro
1               5                  10                  15
Leu Ser Gln Lys Tyr Leu Gln Met Lys Trp Asn Ser Tyr Gly Lys Tyr
            20                  25                  30
Phe His Leu Ala Asn Leu Leu Ile Tyr Ser Ile Phe Leu Val Phe Val
        35                  40                  45
Thr Ile Tyr Ser Ser Leu Met Met Asn Asn Ile Glu Leu Lys Ala Gly
    50                  55                  60
Asp Asn Lys Thr Met Ser Gln Tyr Cys Asn Met Gly Trp Glu Gln Leu
65                  70                  75                  80
Thr Met Asn Leu Ser Gln Asn Pro Ser Val Ala Ser Gln Ile Arg Leu
                85                  90                  95
Asp Ser Cys Glu Glu Arg Ile Asn Arg Thr Thr Ala Ile Leu Phe Cys
            100                 105                 110
Ala Val Ile Val Val Tyr Ile Leu Leu Asn Ser Met Arg Glu Leu
        115                 120                 125
Ile Gln Ile Tyr Gln Gln Lys Leu His Tyr Ile Leu Glu Thr Val Asn
    130                 135                 140
Leu Ile Ser Trp Val Leu Tyr Ile Ser Ala Leu Val Met Val Thr Pro
145                 150                 155                 160
Ala Phe Gln Pro Asp Gly Gly Ile Asn Thr Ile His Tyr Ser Ala Ala
                165                 170                 175
Ser Ile Ala Val Phe Leu Ser Trp Phe Arg Leu Leu Leu Phe Leu Gln
            180                 185                 190
Arg Phe Asp Gln Val Gly Ile Tyr Val Val Met Phe Leu Glu Ile Leu
        195                 200                 205
Gln Thr Leu Ile Lys Val Leu Met Val Phe Ser Ile Leu Ile Ile Ala
    210                 215                 220
Phe Gly Leu Ala Phe Tyr Ile Leu Leu Ser Lys Ile Ile Asp Pro Gln
225                 230                 235                 240
Pro Asn His Leu Ser Phe Ser Asn Ile Pro Met Ser Leu Leu Arg Thr
                245                 250                 255
Phe Ser Met Met Leu Gly Glu Leu Asp Phe Val Gly Thr Tyr Val Asn
            260                 265                 270
Thr Tyr Tyr Arg Asp Gln Leu Lys Val Pro Met Thr Ser Phe Leu Ile
        275                 280                 285
Leu Ser Val Phe Met Ile Leu Met Pro Ile Leu Leu Met Asn Leu Leu
    290                 295                 300
Ile Gly Leu Ala Val Gly Asp Ile Glu Ser Val Arg Arg Asn Ala Gln
305                 310                 315                 320
Leu Lys Arg Leu Ala Met Gln Val Val Leu His Thr Glu Leu Glu Arg
                325                 330                 335
Lys Leu Pro His Val Trp Leu Gln Arg Val Asp Lys Met Glu Leu Ile
            340                 345                 350
```

<210> SEQ ID NO 4
<211> LENGTH: 368
<212> TYPE: PRT
<213> ORGANISM: Drosophila melanogaster

<400> SEQUENCE: 4

```
Leu Asp Val Leu Ile Glu Asn Glu Gln Lys Glu Val Ile Ala His Thr
```

```
                1               5                    10                   15
            Val Val Gln Arg Tyr Leu Gln Glu Leu Trp His Gly Ser Leu Thr Trp
                            20                  25                  30

Ala Ser Trp Lys Ile Leu Leu Leu Val Ala Phe Ile Val Cys Pro
                        35                  40                  45

Pro Val Trp Ile Gly Phe Thr Phe Pro Met Gly His Lys Phe Asn Lys
                        50                  55                  60

Val Pro Ile Ile Lys Phe Met Ser Tyr Leu Thr Ser His Ile Tyr Leu
            65                  70                  75                  80

Met Ile His Leu Ser Ile Val Gly Ile Thr Pro Ile Tyr Pro Val Leu
                            85                  90                  95

Arg Leu Ser Leu Val Pro Tyr Trp Tyr Glu Val Gly Leu Leu Ile Trp
                        100                 105                 110

Leu Ser Gly Leu Leu Leu Phe Glu Leu Thr Asn Pro Ser Asp Lys Ser
                        115                 120                 125

Gly Leu Gly Ser Ile Lys Val Leu Val Leu Leu Gly Met Ala Gly
                        130                 135                 140

Val Gly Val His Val Ser Ala Phe Leu Phe Val Ser Lys Glu Tyr Trp
            145                 150                 155                 160

Pro Thr Leu Val Tyr Cys Arg Asn Gln Cys Phe Ala Leu Ala Phe Leu
                        165                 170                 175

Leu Ala Cys Val Gln Ile Leu Asp Phe Leu Ser Phe His His Leu Phe
                        180                 185                 190

Gly Pro Trp Ala Ile Ile Gly Asp Leu Leu Lys Asp Leu Ala Arg
                        195                 200                 205

Phe Leu Ala Val Leu Ala Ile Phe Val Phe Gly Phe Ser Met His Ile
                        210                 215                 220

Val Ala Leu Asn Gln Ser Phe Ala Asn Phe Ser Pro Glu Asp Leu Arg
            225                 230                 235                 240

Ser Phe Glu Lys Lys Asn Arg Asn Arg Gly Tyr Phe Ser Asp Val Arg
                        245                 250                 255

Met His Pro Ile Asn Ser Phe Glu Leu Leu Phe Phe Ala Val Phe Gly
                        260                 265                 270

Gln Thr Thr Thr Glu Gln Thr Gln Val Asp Lys Ile Lys Asn Val Ala
                        275                 280                 285

Thr Pro Thr Gln Pro Tyr Trp Val Glu Tyr Leu Phe Lys Ile Val Phe
                        290                 295                 300

Gly Ile Tyr Met Leu Val Ser Val Val Leu Ile Asn Leu Leu Ile
            305                 310                 315                 320

Ala Met Met Ser Asp Thr Tyr Gln Arg Ile Gln Val Val Leu Leu Asn
                        325                 330                 335

Ala Leu Leu Ser Asn Ser Thr Leu Phe Ile Asn Ser Tyr Phe Asn His
                        340                 345                 350

Lys Tyr Ile Asn Phe Ile Leu His Cys Val Leu Ile Leu Tyr Phe
                        355                 360                 365

<210> SEQ ID NO 5
            <211> LENGTH: 365
            <212> TYPE: PRT
            <213> ORGANISM: Caenorhabditis elegans

<400> SEQUENCE: 5

Leu Asp Val Leu Ile Glu Asn Glu Gln Lys Glu Val Val Ser Tyr Ala
            1               5                   10                  15
```

```
Ser Val Gln Arg Tyr Leu Thr Glu Val Trp Thr Ala Arg Val Asp Trp
         20                  25                  30

Ser Phe Gly Lys Phe Val Ala Phe Ser Leu Phe Val Leu Ile Cys Pro
         35                  40                  45

Pro Ala Trp Phe Tyr Phe Ser Leu Pro Leu Asp Ser Arg Ile Gly Arg
50                       55                  60

Ala Pro Ile Ile Lys Phe Val Cys His Ile Val Ser His Val Tyr Phe
65                  70                  75                  80

Thr Ile Leu Leu Thr Ile Val Val Leu Asn Ile Thr His Lys Met Tyr
                 85                  90                  95

Glu Val Thr Ser Val Val Pro Asn Pro Val Glu Trp Leu Leu Leu Leu
             100                 105                 110

Trp Leu Ser Gly Asn Leu Val Ser Glu Leu Ser Thr Val Gly Gly Gly
         115                 120                 125

Ser Gly Leu Gly Ile Val Lys Val Leu Ile Leu Val Leu Ser Ala Met
130                 135                 140

Ala Ile Ala Val His Val Leu Ala Phe Leu Leu Pro Ala Val Phe Leu
145                 150                 155                 160

Thr His Leu Asp Asn Asp Glu Lys Leu His Phe Ala Arg Thr Met Leu
                 165                 170                 175

Tyr Leu Lys Asn Gln Leu Phe Ala Phe Ala Leu Leu Phe Ala Phe Val
             180                 185                 190

Glu Tyr Leu Asp Phe Leu Thr Val His His Leu Phe Gly Pro Trp Ala
         195                 200                 205

Ile Ile Ile Arg Asp Leu Met Tyr Asp Leu Ala Arg Phe Leu Val Ile
210                 215                 220

Leu Met Leu Phe Val Ala Gly Phe Thr Leu His Val Thr Ser Ile Phe
225                 230                 235                 240

Gln Pro Ala Tyr Gln Pro Val Asp Glu Asp Ser Ala Glu Leu Met Arg
                 245                 250                 255

Leu Ala Ser Pro Ser Gln Thr Leu Glu Met Leu Phe Phe Ser Leu Phe
             260                 265                 270

Gly Leu Val Glu Pro Asp Ser Met Pro Pro Leu His Leu Val Pro Asp
         275                 280                 285

Phe Ala Lys Ile Ile Leu Lys Leu Leu Phe Gly Ile Tyr Met Met Val
290                 295                 300

Thr Leu Ile Val Leu Ile Asn Leu Leu Ile Ala Met Met Ser Asp Thr
305                 310                 315                 320

Tyr Gln Arg Ile Gln Ala Gln Ser Asp Lys Glu Trp Lys Phe Gly Arg
                 325                 330                 335

Ala Ile Leu Ile Arg Gln Met Asn Lys Lys Ser Ala Thr Pro Ser Pro
             340                 345                 350

Ile Asn Met Leu Thr Lys Leu Ile Ile Val Leu Arg Val
         355                 360                 365

<210> SEQ ID NO 6
<211> LENGTH: 331
<212> TYPE: PRT
<213> ORGANISM: Caenorhabditis elegans

<400> SEQUENCE: 6

Leu Lys Leu Met Ala Asp Ala Glu Lys Leu His Leu Leu Asn His Pro
1               5                   10                  15

Leu Ser Lys Ala Leu Leu Lys Tyr Lys Trp Asn Arg Leu Gly Arg Pro
             20                  25                  30
```

```
Met Tyr Tyr Phe Ala Leu Phe Met Tyr Leu Val Phe Ile Val Ser Leu
             35                  40                  45

Thr Gln Tyr Val Arg His Thr Lys Ala Pro Tyr Asn Val Trp Asn Glu
 50                  55                  60

Glu Ser Tyr Tyr Asp Ser Glu Tyr Phe Asp Glu Asn Glu Thr Cys Pro
 65                  70                  75                  80

Gln Ile Asn Thr Thr Lys Pro Asp Val Val Trp Lys Ile Ile Ile Gln
                 85                  90                  95

Thr Leu Ala Val Cys Gln Ile Leu Val Glu Cys Phe Gln Leu Phe Gln
                100                 105                 110

Arg Lys Phe Ala Tyr Leu Val Asn Trp Glu Asn Trp Ile Asp Cys Phe
            115                 120                 125

Ile Tyr Ser Thr Ala Leu Ile Thr Val Tyr Asp Phe Ser Glu Cys Ser
        130                 135                 140

Ala Thr Ser Gly Val Arg Gln Asn Trp Gln Trp Ile Leu Ala Ala Leu
145                 150                 155                 160

Cys Ile Phe Phe Gly Trp Ile Asn Leu Leu Phe Met Ile Arg Lys Met
                165                 170                 175

Pro Arg Phe Gly Ile Phe Val Val Met Phe Val Asp Ile Val Lys Thr
                180                 185                 190

Phe Phe Arg Phe Phe Pro Val Phe Val Leu Phe Ile Ile Ala Phe Ser
            195                 200                 205

Ser Ser Phe Tyr Val Ile Leu Gln Asn Arg Pro Glu Phe Ser Thr Ile
        210                 215                 220

Phe Met Ser Pro Leu Lys Thr Thr Val Met Met Ile Gly Glu Phe Glu
225                 230                 235                 240

Phe Thr Gly Ile Phe His Gly Asp Glu Thr Thr His Ala Glu Lys Met
                245                 250                 255

Phe Gly Pro Ala His Thr Ala Val Ala Cys Ala Leu Phe Phe Phe Phe
                260                 265                 270

Cys Ile Ile Met Thr Ile Leu Leu Met Asn Leu Leu Val Gly Leu Ala
            275                 280                 285

Val Asp Asp Ile Lys Gly Val Gln Glu Lys Ala Glu Leu Lys Arg Leu
290                 295                 300

Ala Met Gln Val Asp Leu Val Leu Gln Ile Glu Ala Ser Leu His Phe
305                 310                 315                 320

Phe Ile Gln Arg Thr Lys Lys Tyr Ala Thr Cys
                325                 330

<210> SEQ ID NO 7
<211> LENGTH: 333
<212> TYPE: PRT
<213> ORGANISM: Drosophila melanogaster

<400> SEQUENCE: 7

Leu Asn Thr Phe Val Asp Glu Gly Gln Lys Glu Ile Leu Glu His Pro
1                5                  10                  15

Leu Cys Ser Ser Phe Leu Tyr Ile Lys Trp Gly Lys Ile Arg Lys Tyr
                 20                  25                  30

Tyr Ile Gly Arg Leu Ile Phe Cys Phe Ser Phe Val Leu Phe Leu Thr
            35                  40                  45

Leu Tyr Val Leu Thr Ala Leu Ala His Asn Cys Tyr Asn Gly Ser Lys
 50                  55                  60

Asn Asp Asn Thr Thr Ile Pro Ala Gln Glu Leu Cys Gln Lys Gln Ser
```

```
                65                  70                  75                  80
Ile Leu Gly Asp Met Leu Arg Asn Asn Pro Phe Val Met Glu Met Gln
                    85                  90                  95
Trp Trp Val Leu Val Ala Ile Thr Ile Val Glu Ile Phe Arg Lys Leu
                100                 105                 110
Tyr Gly Ile Thr Gly Tyr Ser Ser Phe Arg His Tyr Val Thr Gln Val
                115                 120                 125
Glu Asn Ile Met Glu Trp Phe Val Ile Thr Ser Val Phe Val Ile Ser
                130                 135                 140
Tyr Ile Tyr Thr Asn Lys Thr Tyr Thr Phe Gln Asn His Ile Gly Ala
145                 150                 155                 160
Phe Ala Val Leu Leu Gly Trp Thr Asn Leu Met Leu Met Ile Gly Gln
                165                 170                 175
Leu Pro Val Phe Asp Val Tyr Val Ala Met Tyr Thr Arg Val Gln Gly
                180                 185                 190
Glu Phe Ala Lys Leu Phe Met Ala Tyr Ser Cys Met Leu Ile Gly Phe
                195                 200                 205
Thr Ile Ser Phe Cys Val Ile Phe Pro Ser Ser Ser Ser Phe Ala Asn
                210                 215                 220
Pro Phe Met Gly Phe Ile Thr Val Leu Val Met Met Ile Gly Glu Gln
225                 230                 235                 240
Asp Leu Ser Leu Leu Ile Asn Asp Pro Glu Gly Lys Asp Pro Pro Phe
                245                 250                 255
Leu Leu Glu Val Ser Ala Gln Ile Thr Phe Val Leu Phe Leu Leu Phe
                260                 265                 270
Val Thr Ile Ile Leu Met Asn Leu Leu Val Gly Ile Ala Val His Asp
                275                 280                 285
Ile Gln Gly Leu Lys Lys Thr Ala Gly Leu Ser Lys Leu Val Arg Gln
                290                 295                 300
Thr Lys Leu Ile Ser Tyr Ile Glu Ser Ala Leu Phe Asn Gly Tyr Leu
305                 310                 315                 320
Pro Thr Trp Leu Arg Asn Leu Leu His Tyr Thr Ala Leu
                325                 330

<210> SEQ ID NO 8
<211> LENGTH: 314
<212> TYPE: PRT
<213> ORGANISM: Drosophila melanogaster

<400> SEQUENCE: 8

Leu Leu Ser Leu Ile Glu Val Gly Gln Lys Arg Ile Leu Met His Pro
1               5                   10                  15
Leu Cys Glu Thr Phe Leu Phe Leu Lys Trp Arg Arg Ile Arg Lys Phe
                20                  25                  30
Phe Leu Met Ser Leu Ala Tyr His Thr Leu Phe Val Ile Leu Phe Thr
                35                  40                  45
Phe Tyr Val Ile Trp Val Tyr Val Arg Cys Cys Lys Lys Glu Glu Leu
                50                  55                  60
Cys Val Ala Pro Gly Tyr Val Ser Thr Ile Gly Tyr Leu Val Ile Ile
65                  70                  75                  80
Leu Asn Leu Ile Leu Leu Gly Lys Glu Val Phe Gln Met Ala His Gly
                85                  90                  95
Leu Arg Gly Tyr Ala Lys Tyr Trp Glu Asn Trp Leu Gln Trp Thr Ile
                100                 105                 110
```

Gly Thr Gly Val Leu Leu Cys Val Thr Pro Glu Thr Val Arg Thr Asp
            115                 120                 125

Asp Leu Thr Ala Val Pro Val Trp Gln His His Val Ala Ala Ile Val
130                 135                 140

Ile Leu Leu Val Trp Leu Glu Leu Met Met Leu Val Gly Arg Phe Pro
145                 150                 155                 160

Ile Phe Gly Val Tyr Val Gln Met Phe Thr Lys Val Ala Val Asn Phe
                165                 170                 175

Ala Lys Phe Leu Leu Ala Tyr Ile Cys Leu Leu Val Ala Phe Gly Leu
            180                 185                 190

Ser Phe Ala Val Leu Phe Asn Asp Tyr Pro Ala Phe Glu Asn Ile Thr
        195                 200                 205

Trp Ser Phe Leu Lys Ser Ile Thr Met Met Ser Gly Glu Leu Glu Phe
210                 215                 220

Glu Asp Ile Phe Tyr Gly Asp Tyr Ala Val Lys Phe Pro Val Thr Ala
225                 230                 235                 240

His Ile Ile Phe Leu Ser Phe Val Leu Leu Val Thr Val Ile Leu Thr
                245                 250                 255

Asn Leu Met Val Gly Leu Ala Val Ser Asp Ile Gln Gly Leu Gln Val
            260                 265                 270

Ser Ala Thr Leu Asp Arg Leu Val Arg Gln Ala Glu Leu Val Ser Arg
        275                 280                 285

Leu Glu Ser Leu Phe Phe Ser Arg Leu Leu Arg Ser Ala Pro Thr Asn
            290                 295                 300

Leu Ile Gln Leu Cys Lys Arg Ser Ala Leu
305                 310

<210> SEQ ID NO 9
<211> LENGTH: 20
<212> TYPE: DNA
<213> ORGANISM: Artificial sequence
<220> FEATURE:
<223> OTHER INFORMATION: Primer

<400> SEQUENCE: 9
agtggggaga ctaccctgtg                                           20

<210> SEQ ID NO 10
<211> LENGTH: 21
<212> TYPE: DNA
<213> ORGANISM: Artificial sequence
<220> FEATURE:
<223> OTHER INFORMATION: Primer

<400> SEQUENCE: 10
tttatcatgc ccattctttg c                                         21

<210> SEQ ID NO 11
<211> LENGTH: 36
<212> TYPE: DNA
<213> ORGANISM: Artificial sequence
<220> FEATURE:
<223> OTHER INFORMATION: Primer

<400> SEQUENCE: 11
tttggatccg ccaccatgaa gcgcggcttg aggagg                         36

<210> SEQ ID NO 12
<211> LENGTH: 37
<212> TYPE: DNA

<213> ORGANISM: Artificial sequence
<220> FEATURE:
<223> OTHER INFORMATION: Primer

<400> SEQUENCE: 12
tttgcggccg cctaaaagtc cgggtggcta atagaac        37

<210> SEQ ID NO 13
<211> LENGTH: 3378
<212> TYPE: DNA
<213> ORGANISM: Mus musculus

<400> SEQUENCE: 13

| | | | | | | |
|---|---|---|---|---|---|---|
| atgaagcgcg | gcttgaggag | gattctgctc | ccggaggaaa | ggaaggaggt | ccagggcgtt | 60 |
| gtctatcgcg | gcgtcgggga | agacatggac | tgctccaagg | aatcctttaa | ggtggacatt | 120 |
| gaaggagata | tgtgtagatt | agaagacttc | atcaagaacc | gaagaaaact | aagcaaatat | 180 |
| gaggatgaaa | atctctgtcc | tctgcatcac | gcagcagcag | aaggtcaagt | tgaactgatg | 240 |
| gaactgatca | tcaatggttc | ttcgtgtgaa | gtgctgaata | taatggatgg | ttatggaaat | 300 |
| accccactgc | attgtgctgc | agaaaaaaat | caagttgaaa | gtgtaaagtt | tcttctcagc | 360 |
| caaggagcaa | atccaaacct | ccgaaataga | acatgatgt | caccccttca | catagctgtg | 420 |
| catggcatgt | acaacgaagt | gatcaaggtg | ttgactgagc | acaaggccac | taacatcaat | 480 |
| ttagaaggag | agaatgggaa | cacggctttg | atgtccacgt | gtgccaaaga | caacagtgaa | 540 |
| gctttgcaaa | ttttgttaga | aaaaggagct | aagctgtgta | aatcaaataa | gtggggagac | 600 |
| taccctgtgc | accaggcagc | attttcaggt | gccaaaaaat | gcatggaatt | aatcttagca | 660 |
| tatggtgaaa | agaacggcta | cagcagggag | actcacatta | attttgtgaa | tcacaagaaa | 720 |
| gccagccctc | tccacctagc | agttcaaagc | ggagacttgg | acatgattaa | gatgtgcctg | 780 |
| gacaacggtg | cacacatcga | catgatggag | aatgccaaat | gcatggccct | ccattttgct | 840 |
| gcaacccagg | gagccactga | catcgttaag | ctcatgatct | catcctatac | cggaagtagt | 900 |
| gatattgtga | atgcagttga | tgcaatcag | gagaccctgc | ttcacagagc | tcgttatttt | 960 |
| gatcaccatg | acctggcaga | atacctaata | tcagtgggag | cagacatcaa | cagcactgat | 1020 |
| tctgaaggac | gctctccact | tatttttagca | acagcttctg | catcctggaa | cattgtgaat | 1080 |
| ttgctcctct | gtaaaggtgc | caaagtagac | ataaaagatc | atcttggacg | taactttttg | 1140 |
| catttgactg | tgcagcagcc | ttatggacta | agaaatttgc | ggcctgagtt | tatgcagatg | 1200 |
| caacacatca | aagagctggt | gatggatgaa | gacaatgacg | atgcacacc | tctccattat | 1260 |
| gcctgtaggc | aggggggttcc | tgtctctgta | ataacctcc | ttggcttcaa | tgtgtccatt | 1320 |
| catagcaaaa | gtaaagataa | gaagtcgccc | ctgcattttg | cagccagtta | tgggcgcatc | 1380 |
| aatacatgtc | agagacttct | gcaagacata | agtgatacga | ggcttttgaa | tgaaggggat | 1440 |
| ctccatggga | tgaccctct | ccacctggca | gcaaaaatg | gcatgataaa | agtcgttcaa | 1500 |
| ctccttctga | gaaaggggc | cttatttctc | agtgaccaca | atggctggac | tgctttgcat | 1560 |
| cacgcctcca | tgggtgggta | cactcagacc | atgaaggtca | ttcttgatac | taacttgaaa | 1620 |
| tgcacagacc | gactagatga | agaagggaac | acagcactcc | actttgcagc | acgggaaggc | 1680 |
| catgccaagc | tgttgcaat | gcttttgagc | tacaatgctg | acatcctcct | gaacaagaag | 1740 |
| caagcttcct | ttctgcatat | tgccctgcac | aataagcgca | aggaagtggt | tctcacaacc | 1800 |
| atcagaaata | aagatgggga | tgagtgtctt | caagttttca | ctcataattc | tccaagcaat | 1860 |
| cgatgtccaa | tcatggagat | ggtagaatac | ctccccgagt | gcatgaaagt | tcttttagat | 1920 |

-continued

```
ttctgcatga taccttccac agaagacaag tcctgtcaag actaccatat tgagtataat    1980
ttcaagtatc tccaatgccc attatccatg accaaaaaag tagcacctac ccaggatgtg    2040
gtatatgagc ctcttacaat cctcaatgtc atggtccaac ataaccgcat agaactcctc    2100
aaccaccctg tgtgtaggga gtacttactc atgaaatggt gtgcctatgg attcagggcc    2160
catatgatga acctaggatc ttattgtctt ggtctcatac ccatgaccct tcttgttgtc    2220
aaaatacagc ctggaatggc cttcaattct actggaataa tcaatggaac tagtagtact    2280
catgaggaaa gaatagacac tctgaattca tttccaataa aaatatgtat gattctagtt    2340
tttttatcaa gtatatttgg atattgcaaa gaagtgatcc aaattttcca acagaaaagg    2400
aattacttcc tggattacaa caatgctctg gaatgggtta tctatacaac tagtatcatc    2460
ttcgtgttgc ccttgttcct caacatccca gcgtatatgc agtggcaatg tggagcaata    2520
gcgatattct tctactggat gaacttccta ctgtatcttc aaaggtttga gaactgtgga    2580
attttcattg ttatgttgga ggtgattttt aaaacattgc tgagatcgac cggagtgttt    2640
atcttcctcc tactggcttt tggcctcagc tttatgttc tcctgaattt ccaagatgcc    2700
ttcagcaccc cattgctttc cttaatccag acattcagta tgatgctagg agacatcaat    2760
tatcgagatg ccttcctaga accattgttt agaaatgagt tggcataccc agtcctgacc    2820
tttgggcagc ttattgcctt cacaatgttt gtcccaattg ttctcatgaa cttactgatt    2880
ggcttggcgg ttggggacat tgctgaggtc cagaagcatg cgtcattgaa gaggattgct    2940
atgcaggtgg aacttcatac caacttagaa aaaaagctgc cactctggta cttacgcaaa    3000
gtggatcaga ggtccaccat cgtgtatcca aatagaccca ggcacggcag gatgctacgg    3060 tttttttcatt actttcttaa tatgcaagaa acacgacaag aagtaccaaa cattgacaca    3120
tgcttggaaa tggaaatatt gaaacagaaa tatcggctga aggacctcac ttccctcttg    3180
gaaaagcagc atgagctcat caaactcatc atccagaaga tggagatcat ctcagagaca    3240
gaagatgaag ataaccattg ctctttccaa gacaggttca agaaggagag gctggaacag    3300
atgcacagca gtggaatttt tgtcttaaac gcagttaaga ctaaaacaca ttgttctatt    3360
agccacccgg acttttag                                                 3378
```